(12) United States Patent
Stickney

(10) Patent No.: US 11,974,852 B2
(45) Date of Patent: May 7, 2024

(54) DEVICES AND METHODS FOR ANALYZING ELECTROCARDIOGRAM (ECG) SIGNALS FOR ARTIFACT AND NOTIFICATION OF CULPRIT ELECTRODE

(71) Applicant: Physio-Control, Inc., Redmond, WA (US)

(72) Inventor: Ronald E. Stickney, Edmonds, WA (US)

(73) Assignee: Physio-Control, Inc., Redmond, WA (US)

( * ) Notice: Subject to any disclaimer, the term of this patent is extended or adjusted under 35 U.S.C. 154(b) by 294 days.

(21) Appl. No.: 17/066,099

(22) Filed: Oct. 8, 2020

(65) Prior Publication Data

US 2021/0106246 A1    Apr. 15, 2021

Related U.S. Application Data

(60) Provisional application No. 62/914,062, filed on Oct. 11, 2019.

(51) Int. Cl.
*A61B 5/316*    (2021.01)
*A61B 5/00*    (2006.01)
(Continued)

(52) U.S. Cl.
CPC .............. *A61B 5/316* (2021.01); *A61B 5/282* (2021.01); *A61B 5/352* (2021.01); *A61B 5/7207* (2013.01);
(Continued)

(58) Field of Classification Search
CPC ..... A61B 5/352; A61B 5/7207; A61B 5/7217; A61B 5/7221
See application file for complete search history.

(56) References Cited

U.S. PATENT DOCUMENTS 5,983,127 A    11/1999  dePinto
8,805,482 B2 *  8/2014  Sitzman ................. A61B 5/318
                                                    600/509
(Continued)

FOREIGN PATENT DOCUMENTS

WO    WO-2015171804 A1 *  11/2015  ......... A61B 5/04014

OTHER PUBLICATIONS

MacFarlane et al., "Comprehensive Electrocardiology", 2010, Springer, London, United Kingdom, pp. 377-378 (Year: 2010).*
(Continued)

*Primary Examiner* — Yingchuan Zhang
*Assistant Examiner* — Laura Hodge
(74) *Attorney, Agent, or Firm* — McDonnell Boehnen Hulbert & Berghoff LLP

(57) ABSTRACT

An example method of analyzing electrocardiogram (ECG) signals includes receiving, at an ECG device, ECG signals from a multi-lead ECG system. The multi-lead ECG system includes multiple electrodes and leads, and each lead of the multi-lead ECG system provides one of the ECG signals and is coupled to more than one of the multiple electrodes, where certain electrodes are coupled to more than one lead. The method also includes detecting artifact in one or more of the ECG signals, classifying the artifact as a type of artifact, determining which leads of the multiple leads contain at least a threshold amount of the type of artifact, for the leads of the multiple leads that contain at least the threshold amount of the type of artifact identifying a common electrode to the leads, and generating a notification by the ECG device indicating that the common electrode is sensing the artifact.

20 Claims, 12 Drawing Sheets

(51) Int. Cl.
  *A61B 5/282*  (2021.01)
  *A61B 5/352*  (2021.01)
  *G16H 40/40*  (2018.01)
  *G16H 40/63*  (2018.01)
  *G16H 50/20*  (2018.01)
  *G16H 50/70*  (2018.01)

(52) U.S. Cl.
  CPC .......... *A61B 5/7217* (2013.01); *A61B 5/7221* (2013.01); *G16H 40/40* (2018.01); *G16H 40/63* (2018.01); *G16H 50/20* (2018.01); *G16H 50/70* (2018.01)

(56) References Cited

U.S. PATENT DOCUMENTS

| | | | |
|---|---|---|---|
| 9,282,911 | B2 | 3/2016 | Stickney et al. |
| 2010/0076330 | A1* | 3/2010 | Kimura ................ A61B 5/4362 600/511 |
| 2018/0242872 | A1* | 8/2018 | Firoozabadi ........... A61B 5/339 |
| 2018/0264258 | A1* | 9/2018 | Cheng ...................... A61B 5/25 |

OTHER PUBLICATIONS

"I Jekova, Detection of electrode interchange in right precordial and posterior ECG leads, 2015, IEEE, Computing in Cardiology Conference (CinC), pp. 1149-1152" (Year: 2015).*
Allen J, Murray A. Assessing ECG signal quality on a coronary care unit. Physiol Meas. 1996; 17:249-58.
Batchvarov VN, Malik M, Camm J. Incorrect electrode cable connection during electrocardiographic recording. Europace. 2007;9:1081-90.
Farrell RM, Young BJ. Effect of lead quality on computerized ECG interpretation. Computers in Cardiology. 2004;31:173-6.
Farrell RM, Rowlandson GI. The effects of noise on computerized electrocardiogram measurements. J Electrocardiol. 2006;39:S165-73.
Silva I, Moody GB, Celi L. Improving the quality of ECGs collected using mobile phones: the PhysioNet/Computing in Cardiology Challenge 2011. Computing in Cardiology. 2011;38:273-6.
Zaunseder S, Huhle R, Malberg H. CinC Challenge—assessing the usability of ECG by ensemble decision trees. Computing in Cardiology. 2011;38:277-80.
Langley P, Di Marco LY, King S, Duncan D, Di Maria C, Duan W, Bojarnejad M, Zheng D, Allen J, Murray A. An algorithm for assessment of quality of ECGs acquired via mobile telephones. Computing in Cardiology. 2011;38:281-4.
Clifford GD, Lopez D, Li Q, Rezek I. Signal quality indices and data fusion for determining acceptability of electrocardiograms collected in noisy ambulatory environments. Computing in Cardiology. 2011;38:285-8.
Maan AC, van Zwet EW, Man SC, Oliveira-Martens SM, Schalij MJ, Swenne CA. Assessment of signal quality and electrode placement in ECGs using a reconstruction matrix. Computing in Cardiology. 2011;38:289-92.
Hayn D, Jammerbund B, Schreier G. ECG quality assessment for patient empowerment in mhealth applications. Computing in Cardiology. 2011;38:353-6.
Liu C, Li P, Zhao L, Liu F, Wang R. Real-time signal quality assessment for ECGs collected using mobile phones. Computing in Cardiology. 2011;38:357-60.
Moody BE. Rule-based methods for ECG quality control. Computing in Cardiology. 2011;38:361-3.
Noponen K, Karsikas M, Tiinanen S, Kortelainen J, Huikuri H, Seppanen T. Electrocardiogram quality classification based on robust best subsets linear prediction error. Computing in Cardiology. 2011;38:365-68.
Xia H, Garcia GA, McBride JC, Sullivan A, De Bock T, Bains J, Wortham DC, Zhao X. Computer algorithms for evaluating the quality of ECGs in real time. Computing in Cardiology. 2011;38:369-72.
Jekova I, Krasteva V, Dotsinsky I, Christov I, Abacherli R. Recognition of diagnostically useful ECG recordings: alert for corrupted or interchanged leads. Computing in Cardiology. 2011;38:429-32.
Johannesen L. Assessment of ECG quality on an Android platform. Computing in Cardiology. 2011;38:433-36.
Kalkstein N, Kinar Y, Na'aman M, Neumark N, Akiva P. Using machine learning to detect problems in ECG data collection. Computing in Cardiology. 2011;38:437-40.
Tat TH, Xiang C, Thiam LE. Physionet Challenge 2011: improving the quality of electrocardiogramata collected using real time QRS-complex and T-wave detection. Computing in Cardiology. 2011;38: 441-4.
Starc V. Could determination of equivalent dipoles from 12 lead ECG help in detection of misplaced electrodes. Computing in Cardiology. 2011;38: 445-8.
Chudáiek V, Zach L, Kužílek J, SpilkaJ, Lhotská L. Simple assessment on Android platform. Computing in Cardiology. 2011;38:449-51.
Kužílek J, Huptych M, Chudáiek V, Spilka J, Lhotská L. Data quality assessment using multistep SVM classification. Computing in Cardiology. 2011;38:453-55.
Clifford GD, Behar J, Li Q, Rezek I. Signal quality indices and data fusion for determining clinical acceptability of electrocardiograms. Physiol Meas. 2012;33:1419-33.
Jekova I, Krasteva V, Christov I, Abacherli R. Threshold-based system for noise detection in multilead ECG recordings. Physiol Meas. 2012;33:1463-77.

* cited by examiner

DEVICES AND METHODS FOR ANALYZING ELECTROCARDIOGRAM (ECG) SIGNALS FOR ARTIFACT AND NOTIFICATION OF CULPRIT ELECTRODE

CROSS-REFERENCE TO RELATED APPLICATION

The present application claims priority to U.S. provisional application No. 62/914,062, filed on Oct. 11, 2019, the entire contents of which are herein incorporated by reference.

BACKGROUND

Electrocardiogram (ECG) artifact, also known as ECG noise, commonly occurs when ECG signals are being acquired and viewed during ECG monitoring or diagnostic electrocardiography. The artifact sometimes obscures the ECG, making it difficult to identify the heart rhythm and heart rate during ECG monitoring, or making it difficult to interpret a diagnostic ECG. ECG artifact can cause these difficulties regardless of whether it is a clinician or an automated algorithm that is attempting to determine the heart rhythm, heart rate, or ECG interpretation. Leadwire reversal is also a problem that sometimes affects ECG quality for diagnostic ECGs. The effect on ECGs is subtle enough that clinicians may not notice it, but lead reversal may have an adverse impact on ECG interpretation.

Clinicians who use ECG devices may not determine in real-time during the ECG a root cause of the artifact and which electrode or electrodes are picking up the artifact. Even if a lead with the artifact can be identified during the ECG, knowing which leads are affected does not necessarily inform the clinician as to which electrode(s) are affected. Similarly, clinicians may not recognize leadwire reversal when it occurs during the ECG either. Therefore, corrective action may not be performed when needed to optimize ECG quality.

SUMMARY

Within examples, methods and systems for analyzing electrocardiogram (ECG) signals are described.

Within examples, methods and systems for determining which electrode(s) of a multi-lead ECG system are sensing an artifact.

The features, functions, and advantages that have been discussed can be achieved independently in various examples or may be combined in yet other examples. Further details of the examples can be seen with reference to the following description and drawings.

BRIEF DESCRIPTION OF THE FIGURES

The novel features believed characteristic of the illustrative examples are set forth in the appended claims. The illustrative examples, however, as well as a preferred mode of use, further objectives and descriptions thereof, will best be understood by reference to the following detailed description of an illustrative example of the present disclosure when read in conjunction with the accompanying drawings, wherein:

DETAILED DESCRIPTION

Disclosed examples will now be described more fully hereinafter with reference to the accompanying drawings, in which some, but not all, of the disclosed examples are shown. Indeed, several different examples may be described and should not be construed as limited to the examples set forth herein. Rather, these examples are described so that this disclosure will be thorough and complete and will fully convey the scope of the disclosure to those skilled in the art.

Within examples, electrode(s) that are a cause of an artifact in an ECG signal, in addition to affected lead(s), are identified by an ECG device analyzing ECG signals. An example method of analyzing ECG signals includes detecting an artifact in one or more of the ECG signals, classifying the artifact as a type of artifact, determining which leads of the multiple leads contain at least a threshold amount of the type of artifact, and for the leads of the multiple leads that contain at least the threshold amount of the type of artifact, identifying a common electrode to the leads. The ECG device then generates a notification by the ECG device indicating that the common electrode is sensing the artifact. For example, if a diagnostic 12-lead ECG is being acquired and the LL electrode has excessive artifact, the artifact will affect eleven of the twelve leads and only lead I will be unaffected. Example methods and devices herein can further inform the device user that the artifact is coming from the LL electrode instead of only informing them that multiple leads are affected. The methods and devices will direct the device user to the electrode(s) that are the source of the artifact so that they can focus their corrective action where it is needed. The methods and devices can also inform the user regarding the type of artifact that is present, and about leadwire reversal when it occurs to enable corrective action to take place at the time of acquiring the ECG signals.

Figure 1:
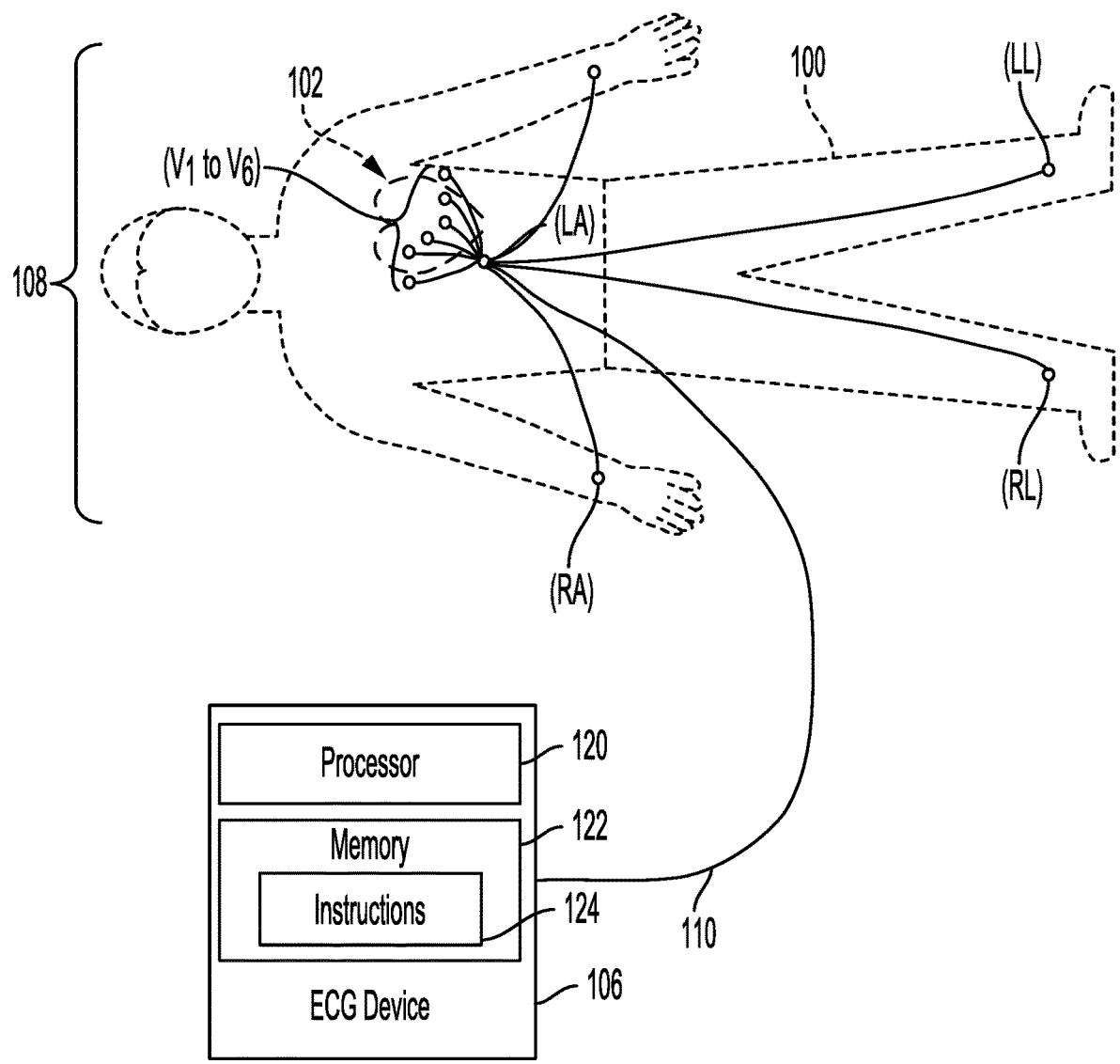
FIG. 1 illustrates a diagram of a defibrillation scene showing use of an external defibrillator to save the life of a person, according to an example implementation.

Referring now to the figures, FIG. 1 illustrates a diagram of a defibrillation scene showing use of an external defibrillator to save the life of a person, according to an example implementation. As shown in FIG. 1, a person 100 is lying on their back. The person 100 could be a patient in a hospital, a clinic, a doctor's office, an ambulance, a public location, a home, or just about anywhere that emergency medical services might be called. The person 100 may be experiencing a condition in their heart 102, or they may be experiencing a different medical problem such as stroke, or they may be getting an ECG for a medical checkup. An ECG device 106 has been brought close to the person 100. The ECG device 106 receives voltage signals from multiple electrodes through leadwire 110, and the ECG device 106 combines the voltage signals in various ways to form multiple ECG leads. Each lead of the ECG device 106 provides one of the ECG signals and is coupled to more than one of the multiple electrodes, and certain electrodes are coupled to more than one lead.

In FIG. 1, the multiple electrodes include ten electrodes, which are labeled $V_1$ to $V_6$ (precordial electrodes), RA (right arm), LA (left arm), RL (right leg), and LL (left leg). A lead is a view of electrical activity of the heart 102 from a particular angle, and in FIG. 1, a 12-lead ECG is shown in which the ten electrodes provide twelve perspectives of activity of the heart 102 using different angles through two electrical planes, namely, frontal and horizontal planes. In FIG. 1, there, a multi-lead ECG system 108 is provided using the voltage signals output by the ten electrodes, for example.

Each of the ten electrodes may be coupled to the person 100 using adhesive and are typically about 2 inches in diameter, for example.

In particular, a 12-lead ECG includes three bipolar limb leads (I, II, and III), augmented limb leads (augmented vector right (aVR), augmented vector left (aVL), and augmented vector foot (aVF)), and six chest leads also called precordial or V leads, (V1, V2, V3, V4, V5, and V6). In this document, precordial electrodes and leadwires will use subscripted numbers in their labels (e.g., $V_1$) and precordial leads will not (e.g., V1).

By using three limb electrodes (RA, LA, and LL), six frontal leads can be derived that provide information about the vertical plane of the heart 102 labeled and derived using the lead equations shown below. The RL electrode is the neutral electrode and is not used in any lead equations.

$$I = LA - RA \qquad \text{Equation (1)}$$

$$II = LL - RA \qquad \text{Equation (2)}$$

$$III = LL - LA \qquad \text{Equation (3)}$$

$$aVR = RA - (LA+LL)/2 \qquad \text{Equation (4)}$$

$$aVL = LA - (RA+LL)/2 \qquad \text{Equation (5)}$$

$$aVF = LL - (LA+RA)/2 \qquad \text{Equation (6)}$$

Limb lead I is taken between a negative electrode placed on the right arm and a positive electrode placed on the left arm; limb lead II between a negative electrode placed on the right arm and a positive electrode placed on the left leg; and so forth. These and the other electrode pairings to form the 12-lead ECG orientations are well known in electrocardiography.

Then, by using the six chest electrodes, six transverse leads can be derived that provide information about the horizontal plane of the heart 102 using the lead equations shown below.

$$V1 = V_1 - (LA+RA+LL)/3 \qquad \text{Equation (7)}$$

$$V2 = V_2 - (LA+RA+LL)/3 \qquad \text{Equation (8)}$$

$$V3 = V_3 - (LA+RA+LL)/3 \qquad \text{Equation (9)}$$

$$V4 = V_4 - (LA+RA+LL)/3 \qquad \text{Equation (10)}$$

$$V5 = V_5 - (LA+RA+LL)/3 \qquad \text{Equation (11)}$$

$$V6 = V_6 - (LA+RA+LL)/3 \qquad \text{Equation (12)}$$

Supplemental V leads are sometimes used and may be any of V3r through V6r on the right side of the chest or V7 through V10 on the back. Equations for those V leads are like the equations for the standard V leads, in general form:

$$Vn = V_n - (LA+RA+LL)/3 \qquad \text{Equation (13)}$$

The ECG device 106 may be an electrocardiograph, which takes a "snapshot" of the 12-lead ECG and is used to detect various cardiac abnormalities. In other examples, the ECG device 106 may be used to continuously or periodically assess the heart rhythm and heart rate. Thus, the ECG device 106 can further include an ECG monitor or other components, such as a processor 120 and memory 122, and optionally a display (not shown). In further examples, the ECG device 106 could be a combined monitor and electrocardiograph. Furthermore, the combined monitor and electrocardiograph could also contain a defibrillator. Thus, in other examples, the ECG device 106 may include an external defibrillator (not shown).

The ECG device 106 may take the form of a computing device with multiple storage partitions and processors for performing functions described herein.

The processor 120 is configured to execute an instance for acquiring the ECG of the person 100. The processor 120 may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on. Thus, the processor 120 may be general-purpose processors or special purpose processors (e.g., digital signal processors, application specific integrated circuits, etc.). The processor 120 may receive inputs from the multi-lead ECG system 108, and process the inputs to generate outputs that are stored in the memory 122.

The memory 122 may be implemented in any number of ways. Such ways include, by way of example and not of limitation, nonvolatile memories (NVM), read-only memories (ROM), random access memories (RAM), any combination of these, etc. In one example, the memory 122 is a non-transitory computer-readable medium having stored therein a plurality of executable instructions 124, which are executable by the processor 120 or other processors that may be included in the ECG device 106. The memory is considered non-transitory computer readable media. In some examples, the memory 122 can be implemented using a single physical device (e.g., one optical, magnetic, organic or other memory or disc storage unit), while in other examples, the memory 122 can be implemented using two or more physical devices.

The processor 120 can be configured to execute the instructions 124 (e.g., computer-readable program instructions) that are stored in the memory 122 and are executable to provide the functionality described herein. Within one example, in operation, when the instructions 124 are executed by the processor 120, the processor 120 is caused to perform functions including to receive ECG signals from the multi-lead ECG system 108, detect an artifact in one or more of the ECG signals, classify the artifact as a type of artifact, based on classifying the artifact as the type of artifact determine which leads of the multiple leads contain at least a threshold amount of the type of artifact, for the leads of the multiple leads that contain at least the threshold amount of the type of artifact identify a common electrode to the leads, and generate a notification indicating that the common electrode is sensing the artifact. Details of these functions are described below.

Figure 2:
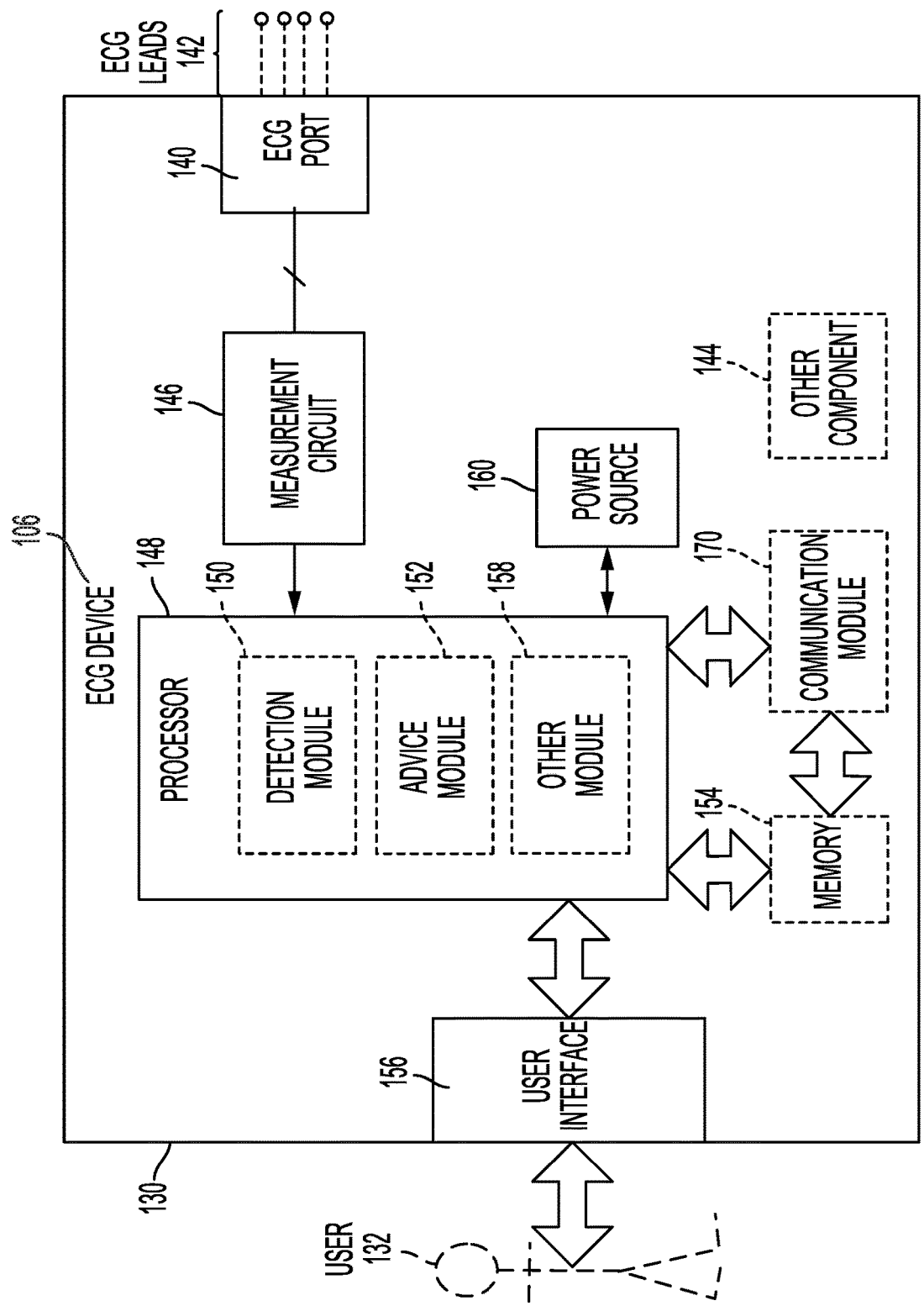
FIG. 2 is a diagram showing example components of the external defibrillator, according to an example implementation.

FIG. 2 is a diagram showing example components of the ECG device 106, according to an example implementation. These components of FIG. 2 can be provided in a housing 130, which is also known as a casing.

The ECG device 106 is intended for use by a user 132, who would be the care provider. The ECG device 106 contains an ECG port 140 in the housing 130, for plugging in ECG leadwires 142. The ECG leadwires 142 can help sense an ECG signal, e.g., a 12-lead signal, or a signal taken from a different number of leads. Moreover, the ECG device 106 could have additional ports (not shown), and another component 144 for the above described additional features, such as for receipt of patient signals.

The ECG device 106 also includes a measurement circuit 146. The measurement circuit 146 receives physiological signals from the ECG port 140, and also from other ports, if provided. These physiological signals are sensed, and information about them is rendered by the measurement circuit 146 as data, or other signals, etc.

The ECG device 106 also includes a processor 148. The processor 148 may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

The processor 148 may include a number of modules. One such module can be a detection module 150, which senses outputs of the measurement circuit 146. The detection module 150 can include an ECG artifact detector.

Another such module in the processor 148 can be an advice module 152, which arrives at a piece of instructional advice based on outputs of the detection module 150. The advice module 152 can include a culprit electrode algorithm residing in a memory unit (not shown) in the advice module 152 for instructing the processor 148 to implement decision rules, etc. Alternatively, the culprit electrode algorithm may reside in part or in whole on a memory 154 of the ECG device 106. The instruction to the processor 148 can be an indication of which electrodes are sensing artifact, and so on. If one or more electrodes are sensing artifact, the processor 148 is configured to report that finding to the user via a user interface 156.

The processor 148 can include additional modules, such as module 158, for other functions. In addition, if the other component 144 is provided, it may be operated in part by the processor 148 or by another processor.

The detection module 150, the advice module 152, and the other module 158 (if included) may take the form of executable instructions stored in the memory 154 and executed by the processor 148 to perform the specific functions of the modules.

Thus, the ECG device 106 further includes the memory 154, which can work together with the processor 148. The memory 154 may be implemented in any number of ways. Such ways include, by way of example and not of limitation, nonvolatile memories (NVM), read-only memories (ROM), random access memories (RAM), any combination of these, etc. The memory 154, if provided, may include programs containing instructions for execution by the processor 148 or other processors that may be included in the ECG device 106. The programs provide instructions for execution by the processor 148, and can also include instructions regarding protocols and decision making analytics, etc. that can be used by the advice module 152. In addition, the memory 154 can store prompts for the user 132, etc. Moreover, the memory 154 can store patient data.

The ECG device 106 may also include a power source 160. To enable portability of the ECG device 106, the power source 160 may include a battery. Such a battery can be implemented as a battery pack, which can be rechargeable or not. Sometimes, a combination is used, of rechargeable and non-rechargeable battery packs. Other examples of the power source 160 can include an AC power override, whereby AC power, instead of power from the power source 160 is delivered to an energy storage module 162 when AC power is available. In some examples, the power source 160 is controlled by the processor 148.

The ECG device 106 further includes the user interface 156 for the user 132. The user interface 156 can be made in any number of ways. For example, the user interface 156 may include a screen, to display a parameter of a patient that is detected and measured, provide visual feedback to the rescuer for their patient care, and so on. The user interface 156 may also include a speaker, to issue voice prompts, etc. The user interface 156 may additionally include various controls, such as pushbuttons, keyboards, and so on. In addition, the discharge circuit 166 can be controlled by the processor 148, or directly by the user 132 via the user interface 156, and so on.

The ECG device 106 can optionally include other components. For example, a communication module 170 may be provided for communicating with other devices. Such communication can be performed wirelessly, or via wire, or by infrared communication, and so on. In this way, data can be communicated from the ECG device 106 to external devices, such as patient data, incident information, therapy attempted, and so on. Thus, the communication module 170 may include a receiver, transmitter, or other hardware to enable communication with the ECG device 106.

The ECG device 106 can implement electrocardiography, which is a technique of acquiring the bioelectrical voltages generated by the heart. These bio-voltages can be detected inside the body or at the skin using the electrodes $V_1$ to $V_6$, RA, LA, RL, and LL. The signals are typically detected using electrodes placed on the body surface. The ECG voltage potential between a pair of electrodes can be acquired and recorded. The ECG voltage can also be acquired as a combination of three or more electrodes. A graphical display of these ECG voltages is known as an electrocardiogram, which is often referred to as an ECG. The ECG is useful in revealing the condition of the heart and to diagnosis heart ailments or disease.

ECG data and patterns from a heart can be defined based upon a number of factors including the number of electrodes that are placed on the human body and where those electrodes are placed. The voltage from a combination of two or more electrodes is known in the art as an ECG lead, as noted above. Over the years, a standard has been established in electrocardiography that specifies ten electrodes placed on a patient configured to define twelve separate leads according to Equations (1)-(12) noted above. Each ECG lead detects the ECG voltage as a combination of two, three, or four of the ten electrodes that form the ECG lead. An orientation of those ECG leads with respect to the heart also provides a directional component to the ECG voltage detected. The ECG voltage together with its directional component form a vector and the display of vectored ECG voltages provides additional information on both magnitude and angle of certain waves in the ECG (e.g., R wave).

However, some challenges exist with obtaining ECG signals. For example, electrocardiogram (ECG) artifact, also known as ECG noise, commonly occurs when ECG signals are being acquired and viewed during ECG monitoring or diagnostic electrocardiography. The artifact sometimes obscures the ECG, making it difficult to identify the heart rhythm and heart rate during ECG monitoring, or making it difficult to interpret a diagnostic ECG. ECG artifact can cause these difficulties regardless of whether it is a clinician or an automated algorithm that is attempting to determine the heart rhythm, heart rate, or ECG interpretation.

Another problem that can occur is leadwire reversal. Leadwire reversal occurs when at least two of the electrodes are interchanged. This results in leads that switch positions, become inverted, are otherwise altered, or remain unchanged (depending on their initial position and vector). The effect on ECGs is subtle enough that clinicians may not notice it, but lead reversal may have an adverse impact on ECG interpretation.

With respect to such problems, clinicians who use ECG devices may not be proficient at determining the root cause of any artifact and which electrode or electrodes are picking up the artifact. Similarly, clinicians commonly fail to recognize leadwire reversal when it occurs. Therefore, they may be unaware of necessary corrective action that is needed to optimize ECG quality.

Some ECG devices include ECG artifact detectors that notify a user when artifact is detected. Some can identify the ECG leads that are affected. However, knowing which leads are affected does not inform the clinician as to which electrode(s) are affected, and many clinicians cannot identify the culprit electrodes when they know the affected leads. For example, if a diagnostic 12-lead ECG is being acquired and the LL electrode has excessive artifact, the artifact will affect eleven of the twelve leads and only Lead I will be unaffected. However, looking at the ECG data, it may be difficult to come to this conclusion in real time.

Within examples herein, cardiac monitor and/or electrocardiograph are programmed to notify users of detected artifact, types of the artifact, lead affected, and electrodes causing the problem. Furthermore, leadwire reversal, if present, is reported before a 12-lead ECG is captured for a 12-lead report.

Thus, examples herein solve a problem of current noise detectors by identifying the affected electrode(s) rather than the affected lead(s). Using the example above, the user can be informed that the artifact is coming from the LL electrode instead of informing them that multiple leads are affected. The device can direct the user to the electrode(s) that are the source of the artifact so that they can focus their corrective action where it is needed. The device can also inform the user regarding the type of artifact that is present, and about leadwire reversal when it occurs.

Figure 3:
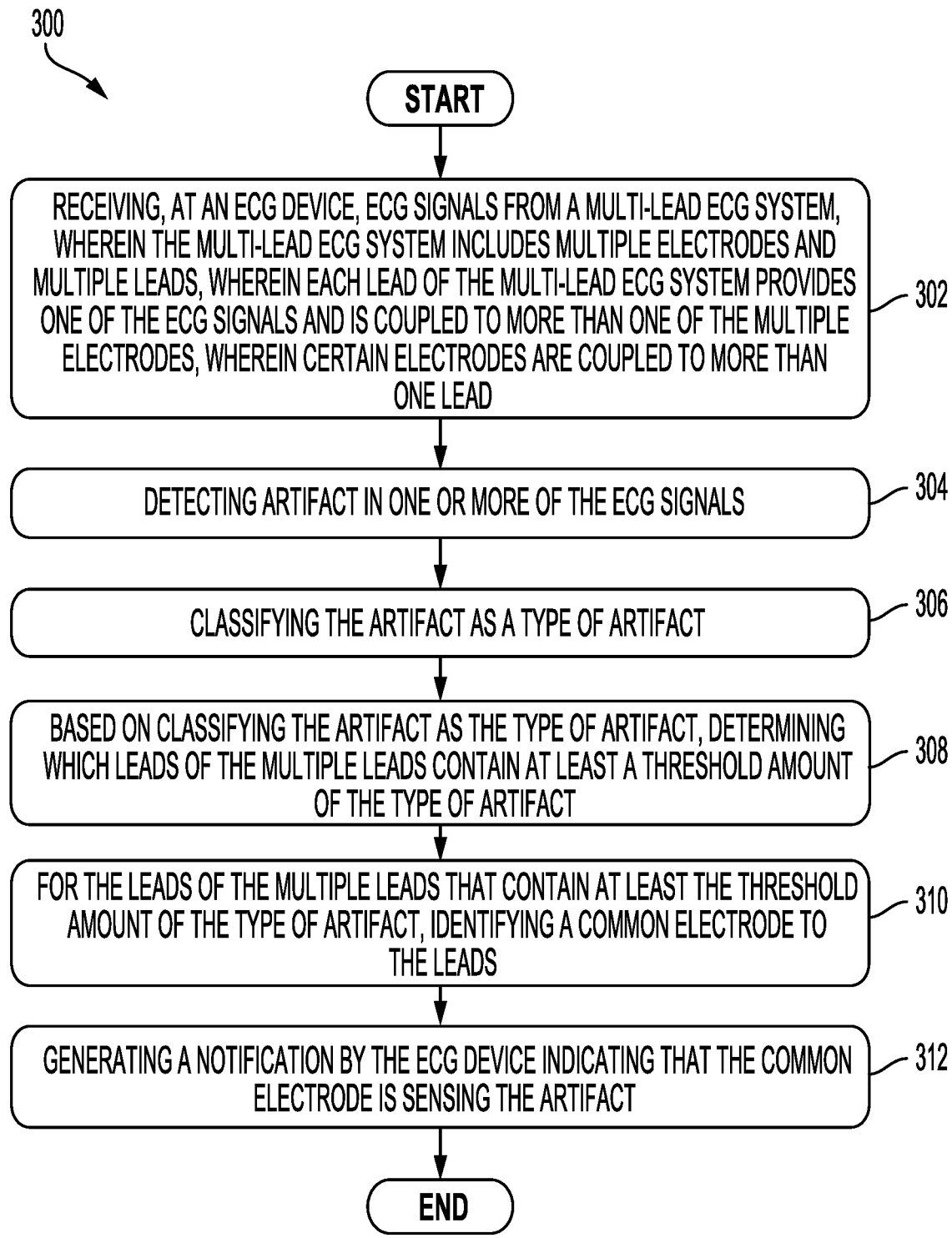
FIG. 3 shows a flowchart of an example of a method of analyzing electrocardiogram (ECG) signals, according to an example implementation.

FIG. 3 shows a flowchart of an example of a method 300 of analyzing electrocardiogram (ECG) signals, according to an example implementation. Method 300 shown in FIG. 2 presents an example of a method that could be used or implemented by the ECG device 106 shown in FIG. 1 or FIG. 2, for example. Further, devices or systems may be used or configured to perform logical functions presented in FIG. 2. In some instances, components of the devices and/or systems may be configured to perform the functions such that the components are actually configured and structured (with hardware and/or software) to enable such performance. In other examples, components of the devices and/or systems may be arranged to be adapted to, capable of, or suited for performing the functions, such as when operated in a specific manner. Method 300 may include one or more operations, functions, or actions as illustrated by one or more of blocks 302-312. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

It should be understood that for this and other processes and methods disclosed herein, flowcharts show functionality and operation of one possible implementation of present examples. In this regard, each block or portions of each block may represent a module, a segment, or a portion of program code, which includes one or more instructions executable by a processor for implementing specific logical functions or steps in the process. The program code may be stored on any type of computer readable medium or data storage, for example, such as a storage device including a disk or hard drive. Further, the program code can be encoded on a computer-readable storage media in a machine-readable format, or on other non-transitory media or articles of manufacture. The computer readable medium may include non-transitory computer readable medium or memory, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a tangible computer readable storage medium, for example.

In addition, each block or portions of each block in FIG. 3, and within other processes and methods disclosed herein, may represent circuitry that is wired to perform the specific logical functions in the process. Alternative implementations are included within the scope of the examples of the present disclosure in which functions may be executed out of order from that shown or discussed, including substantially concurrent or in reverse order, depending on the functionality involved, as would be understood by those reasonably skilled in the art.

At block 302, the method 300 includes receiving, at the ECG device 106, ECG signals from the multi-lead ECG system 108, and the multi-lead ECG system 108 includes multiple electrodes ($V_1$ to $V_6$, RA, LA, RL, and LL) and multiple leads (Leads I, II, III, aVR, aVL, aVF, and V1 to V6), and each lead of the multi-lead ECG system 108 provides one of the ECG signals and is coupled to more than one of the multiple electrodes where certain electrodes are coupled to more than one lead. In some examples, block 302 includes receiving the ECG signals from a 12-lead system with multiple limb leads, multiple augmented limb leads, and multiple precordial leads.

At block 304, the method 300 includes detecting an artifact in one or more of the ECG signals. The ECG device 106 can detect the artifact in the one or more of the ECG signals by digitally sampling a portion of the one or more of the ECG signals, and determining that the digitally sampled portion of the one or more of the ECG signals is outside of a range of acceptable values. The acceptable values can vary based on a number of factors, and below are a number of examples.

In one example, when an ECG amplitude goes above or below a range that a human ECG can nominally reach (e.g., the ECG goes outside 5 mV), an artifact is detected.

In another example, when the ECG has an extremely steep slope not caused by a pacemaker stimulus, such as a slope above 1 mV/msec, an artifact is detected.

In another example, when the ECG baseline goes outside an expected range (e.g., outside 2 mV), an artifact is detected. The baseline may be estimated by running the ECG through a low-pass filter with a cutoff at about 5 Hz.

In another example, when a mean amplitude of the low-pass filtered ECG (e.g., with a cutoff frequency at 2 Hz to preferentially pass motion artifact) is outside an expected range (e.g., outside 5 mV), an artifact is detected.

In another example, when a proportion of ECG samples (e.g., half of samples of the signal) are outside a range (e.g., outside 2 mV), an artifact is detected.

In another example, when a mean amplitude of high-pass filtered ECG (e.g., with a cutoff frequency of 25 Hz to preferentially pass muscle artifact) is outside the normal range (e.g., outside 0.1 mV), an artifact is detected.

In another example, when a standard deviation of the ECG, normalized to the ECG amplitude, exceeds a threshold, an artifact is detected.

In another example, when a skewness (third moment) of the ECG is outside a range, an artifact is detected. This is a measurement of how much the ECG is lopsided (above or below the mean voltage).

In another example, when a kurtosis (fourth moment) of the ECG is outside a range, an artifact is detected. This is a measurement of how much of the ECG is near the extremes rather than near the mean voltage.

In another example, when ECG entropy (randomness) exceeds a threshold, an artifact is detected.

In another example, when a mean amplitude of the ECG after bandpass filtering the ECG to pass only energy near line frequency or a harmonic (multiple) of line frequency is outside the range, an artifact is detected.

In another example, when a number of zero crossings exceed a threshold, such as over five within a several milliseconds time period, an artifact is detected.

In another example, when the number of slope reversals (positive to negative, or vice versa) exceed a threshold, such as over five within a several milliseconds time period, an artifact is detected.

In another example, when a Fast Fourier Transform (FFT) of the ECG has power above a threshold near a line frequency or harmonic of line frequency, an artifact is detected.

In another example, when a FFT of the ECG has power above a threshold in a low frequency range (e.g., 0-2 Hz), an artifact is detected.

In another example, when a FFT of the ECG has power above a threshold in a high frequency range (e.g., above 50 Hz), an artifact is detected.

In another example, when a ratio of power in the 2-50 Hz range to power in the full frequency range is below a threshold, an artifact is detected.

Referring to FIG. 3, at block 306, the method 300 includes classifying the artifact as a type of artifact. It is also useful to the clinician to have an ECG artifact detector that identifies the type of artifact, and there are about five general types of artifact, and further sub-categories of artifact exist as well (e.g., patient moving limb, muscle tension, shivering, shaking, etc.). In one example, block 306 includes classifying the artifact as one of a poor contact artifact, a motion artifact, a muscle artifact, an electromagnetic interference (EMI) artifact, and an electronic stimulator artifact.

A poor contact artifact is most commonly due to the electrode coming partially or wholly detached from the patient, but sometimes due to dried electrode gel, extremely high skin impedance, or an intermittent connection in a signal path from the electrode connector to the ECG device 106. This can cause a large amplitude artifact exceeding 3 millivolts (mV), abrupt steps in the ECG, or intermittent loss of an ECG lead. Thus, when the detected artifact has any of such characteristics, the artifact is classified as a poor contact artifact. Below, FIG. 5 (leads II and III) and FIG. 9 (lead V1) both show poor contact artifact.

A motion artifact is due to patient motion of any type that can cause stretching or bending of the skin under an electrode, which can temporarily change the skin voltage by up to about 3 mV, or 30 mm at standard ECG gain. The motion may be movement by the patient, respiration, movement of the patient by a care provider (e.g., during cardiopulmonary resuscitation), or transport motion (e.g., during ambulance transport). In addition, movement of an electrostatically charged person near the patient can cause small currents to flow through the high impedance of the stratum corneum (dead skin cell layer) under an electrode, resulting in artifact voltages up to ten millivolts (100 mm) or more. Per Ohm's Law, the artifact voltage at an electrode is the current through the stratum corneum multiplied by the impedance of the stratum corneum, and the artifact voltage in an ECG lead is the combination of the artifact voltages from the electrodes that contribute to the lead, as defined in the lead equation (e.g., Equations 1 through 12 above). Motion artifact is usually low frequency artifact (a few Hz or less), but transport can cause medium frequency artifact. For example, wheel shimmy in an ambulance can cause one cycle of ECG artifact for each wheel rotation, causing artifact at a frequency of 15 Hz or more when the ambulance is moving at a typical highway speed. Motion artifact is sometimes described as a wandering baseline in the ECG, such as can occur when patient respiration stretches the skin under an electrode. Thus, when the detected artifact has any of such characteristics, the artifact is classified as a motion artifact. Below, FIGS. 6, 8, and 9 (leads II and III) all show examples of motion artifact.

A muscle artifact is commonly caused by movement by the patient or muscle tension, sometimes caused by muscle tremor. Muscle artifact appears as high frequency artifact, sometimes described as a fuzzy baseline in the ECG. Muscle artifact is also known as electromyogram (EMG) artifact. Thus, when the detected artifact has any of such characteristics, the artifact is classified as a muscle artifact. Below, FIG. 7 (leads I and II) and FIG. 9 (leads I and II) show examples of muscle artifact.

Figure 11A:
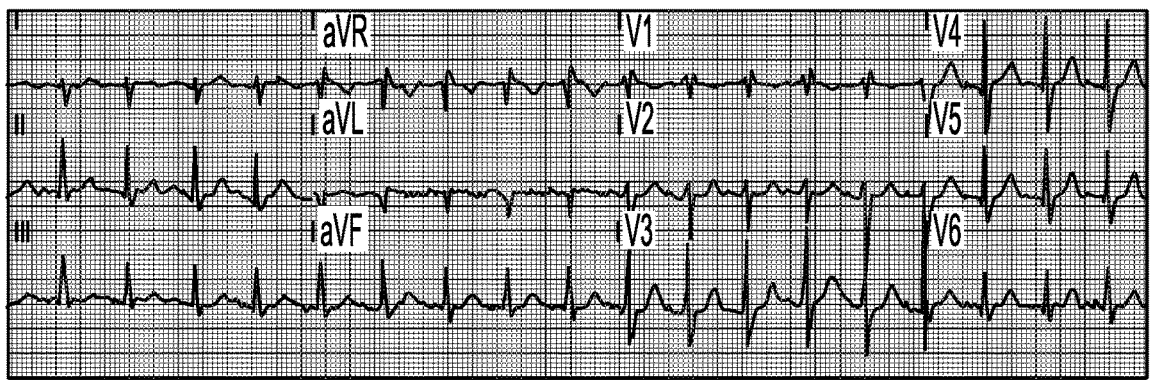
FIG. 11A is an example plot of ECG signals illustrating EMI artifact, according to an example implementation.
Figure 11B:
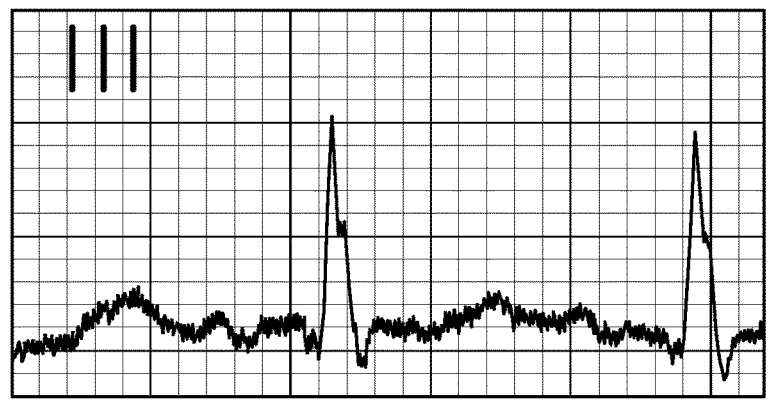
FIG. 11B is an example plot of a portion of lead III magnified illustrating the EMI artifact from FIG. 11A, according to an example implementation.
Figure 11C:
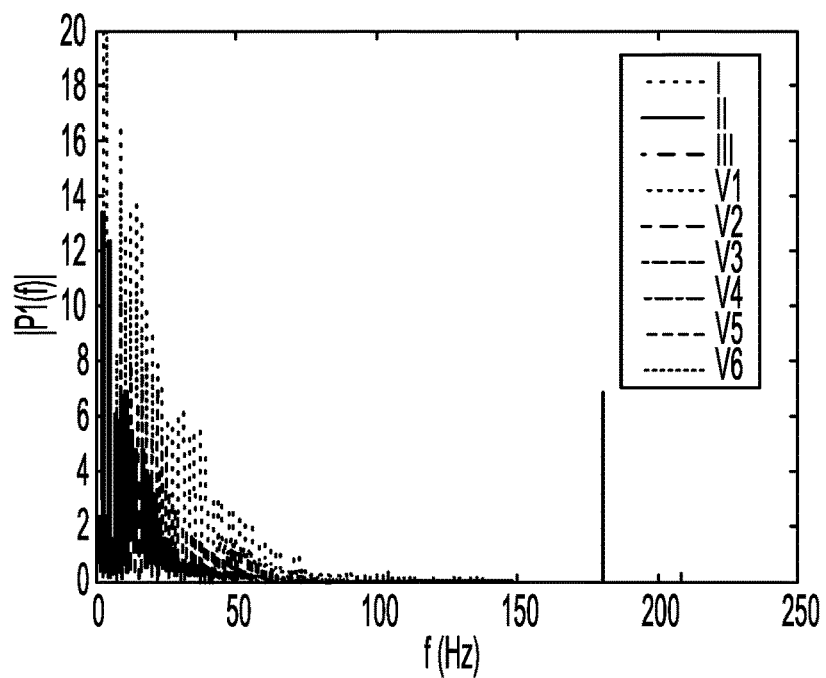
FIG. 11C is an example Fast Fourier Transform (FFT) plot of the ECG signals from FIG. 11A, according to an example implementation.

Electromagnetic interference (EMI) artifact are most often caused by nearby line-powered equipment. The patient can act as an antenna to pick up the EMI. Most commonly, the EMI is at local line frequency, 50 or 60 Hz. Some European electric railroads have a line frequency of 16.7 Hz. Almost all electrocardiographs and ECG monitors suppress the 50 or 60 Hz line frequency, but it can still show up in the ECG if some electrodes are much closer to the source than others, or if the line-powered equipment is turning on and off as with some electric blankets. Ambulances commonly have a power inverter to convert battery voltage to AC power. Pure sine wave inverters generally do not cause problems, but modified sine wave inverters (also known as quasi-sine wave inverters or pulse width modulated inverters) by design radiate EMI at harmonics (multiples) of line frequency (e.g., 120 and/or 180 Hz if the line frequency is 60 Hz). When high frequency (e.g., 50 Hz or higher) EMI is present in the ECG, it can be seen as a thickened baseline in some ECG leads when the ECG is viewed at the full diagnostic frequency response (e.g., with the upper cutoff frequency at 150 Hz). One method for detecting EMI is to use a Fast Fourier Transform (FFT) of the ECG to view it in the frequency domain rather than the time domain. In a FFT plot, power line artifact and various other types of EMI will show up as a spike at the EMI frequency. Thus, when the detected artifact has any of such characteristics, the artifact is classified as an EMI artifact. Below, FIGS. 11A-11C are examples of an ECG with EMI artifact.

Figure 12:
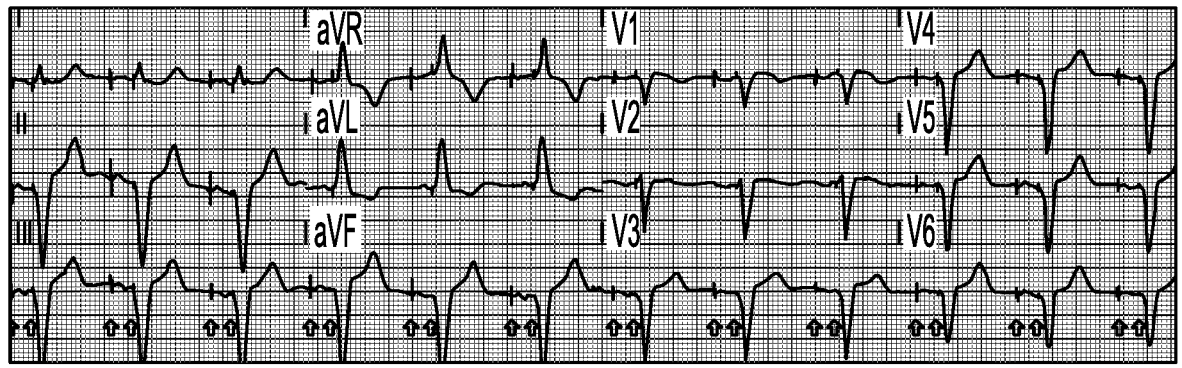
FIG. 12 is an example plot of ECG signals illustrating pacemaker voltage spikes, according to an example implementation.
Figure 13:
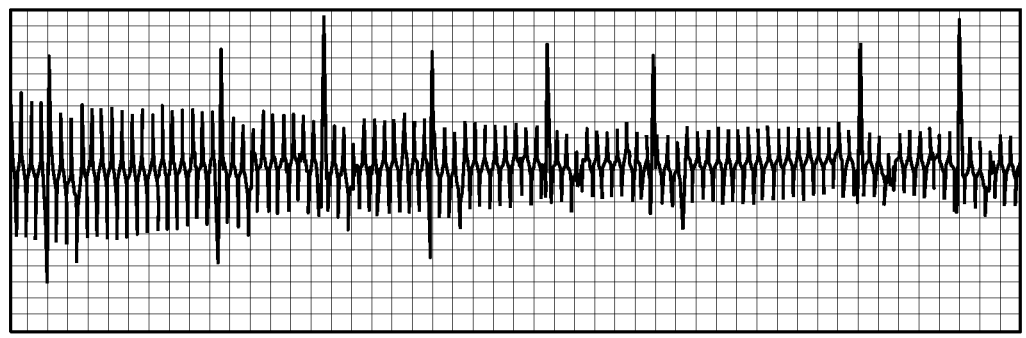
FIG. 13 is an example plot of ECG signals illustrating stimulator artifact, according to an example implementation.

Electronic stimulator artifact generally include voltage spikes from stimulators such as gastric, carotid, or brain stimulators that cause unwanted artifact in the ECG. Voltage spikes from implanted pacemakers are usually considered a signal of interest, however. The artifact typically appears as a narrow spike in the ECG, sometimes often enough to cause multiple spikes per second. Spike amplitude is usually greatest in ECG leads that are largely parallel to the stimulus lead, and smallest in ECG leads that are largely orthogonal to the stimulus lead. Spikes from an electronic stimulator can be detected by looking for a rapid upslope or downslope (i.e., a fast slew rate) in the ECG. For spikes less than 5 ms wide, spike detection can be done in an ECG with a very high sample rate and a very high cutoff frequency. For example, detection of pacemaker spikes is usually done using an ECG signal with a sample rate in the range of 10 kHz to 75 kHz. False detections can be minimized by detecting only spikes within a limited range of durations. For example, almost all implanted pacemaker stimulus spikes are between 0.06 and 2 ms in duration, so spikes that are narrower or wider than that range can be excluded without degrading sensitivity for pacemaker spikes. Thus, when the detected artifact has any of such characteristics, the artifact is classified as an electronic stimulator artifact. Below, FIG. 12 is examples of an ECG with voltage spikes caused by atrial pacing (just prior to the P waves) and ventricular pacing (just prior to the QRS complexes, and FIG. 13 shows an ECG with voltage spikes from a gastric stimulator.

Referring back to FIG. 3, at block 308, the method 300 includes based on classifying the artifact as the type of artifact, determining which leads of the multiple leads contain at least a threshold amount of the type of artifact. The determination includes the ECG device 106 identifying which leads include the artifact characteristics as noted above.

At block 310, the method 300 includes for the leads of the multiple leads that contain at least the threshold amount of the type of artifact, identifying a common electrode to the leads. The ECG device 106 is programmed to utilize Equations (1)-(12) and will determine the common electrode among the leads demonstrating the classified artifact.

At block 312, the method 300 includes generating a notification by the ECG device indicating that the common electrode is sensing the artifact. The notification can be made through a display, or an audio notification. In this manner, the ECG device 106 first determines that artifact is present, then classifies the artifact, then identifies leads affected, and further identifies the culprit electrode causing the problem. The clinician may then readily address the problem in real-time during data collection. Thus, within examples, the method 300 includes the ECG device 106 performing the detecting, classifying, determining, identifying, and generating of the notification continuously as the ECG signals are being received.

It will be useful to device users who are acquiring the ECG to inform them when substantial ECG artifact is present, what types of artifact are present, and which electrodes are picking up the artifact. That will provide actionable feedback to the device user. For example, if the device user is informed that there is muscle artifact at the LL electrode, the device user will be able to take corrective action by getting the patient to relax their left leg.

The ECG device 106 may generate additional notifications as well. For example, the method 300 may also include generating a second notification by the ECG device 106 indicating that the multi-lead ECG system 108 is sensing the artifact. This alerts the clinician that an issue is present. In another example, the method 300 includes generating a second notification by the ECG device 106 indicating the type of artifact.

Sometimes, the ECG signal may include multiple types of artifact, and the method 300 includes detecting multiple different artifacts in the ECG signals, classifying the multiple different artifacts as one of a plurality of types of artifact, mapping leads of the multiple leads that contain at least the threshold amount of one of the multiple different artifacts to a respective one of the plurality of types of artifact so as to form groups of leads, for each group of the groups of leads identifying a respective common electrode to the group, and generating the notification by the ECG device 106 indicating that the respective common electrodes for each group are sensing the respective one of the plurality of types of artifact.

Certain patterns in the ECG can further suggest or be indicative of occurrence of leadwire reversal, which is known to sometimes occur in clinical practice. Within some examples, the method 300 can further include generating a second type of notification by the ECG device indicating a leadwire reversal. In a particular example, the ECG signals are received from the multi-lead ECG system 108 that comprises a 12-lead system with multiple limb leadwires and multiple precordial leadwires, including a left arm (LA) leadwire, a right arm (RA) leadwire, a left leg (LL) leadwire, and a right leg (RL) leadwire, and a type of leadwire reversal is one of LA-RA leadwire reversal, LA-LL leadwire reversal, RA-LL leadwire reversal, RA-RL leadwire reversal, LA-RL leadwire reversal, arm-leg leadwire reversal, and reversal of two precordial leadwires. The ECG device 106 may indicate that a leadwire reversal is present, and also determine and indicate the type of leadwire reversal.

In a particular example, the method 300 can further include identifying a pattern in the ECG signals by comparison of a P wave and a QRS complex in the ECG signals from the multiple leads, and for the leads of the multiple leads in which the pattern is identified, identifying a leadwire reversal. Specifically, a negative P wave in Lead I suggests reversal of the LA and RA leadwires. When P waves are absent, such as with atrial fibrillation, a negative QRS complex and T wave in Lead I while the QRS complex and T wave are positive in leads V5 and V6 also suggests LA-RA reversal.

In another example, the method 300 can further include identifying an R wave amplitude change pattern in the ECG signals from a lead of the multiple precordial leads that includes a pattern other than increasing monotonically from lead V1 to about lead V4 and then decreasing monotonically to lead V6, and for the lead of the multiple leads having the R wave amplitude change pattern other than increasing monotonically and then decreasing monotonically, identifying a leadwire reversal.

Still further, the method 300 can include identifying an S wave amplitude change pattern in the ECG signals from a lead of the multiple precordial leads that includes a pattern other than first decreasing and then increasing, and for the lead of the multiple leads having the S wave amplitude change pattern other than first decreasing and then increasing, identifying a leadwire reversal.

As mentioned, the method 300 may be executed by the ECG device 106 while signals are being acquired and on a continuous basis. In other examples, the method 300 can be adjusted to be executed on previously acquired ECG signals to assess ECG quality in a batch of ECGs.

Figure 4A:
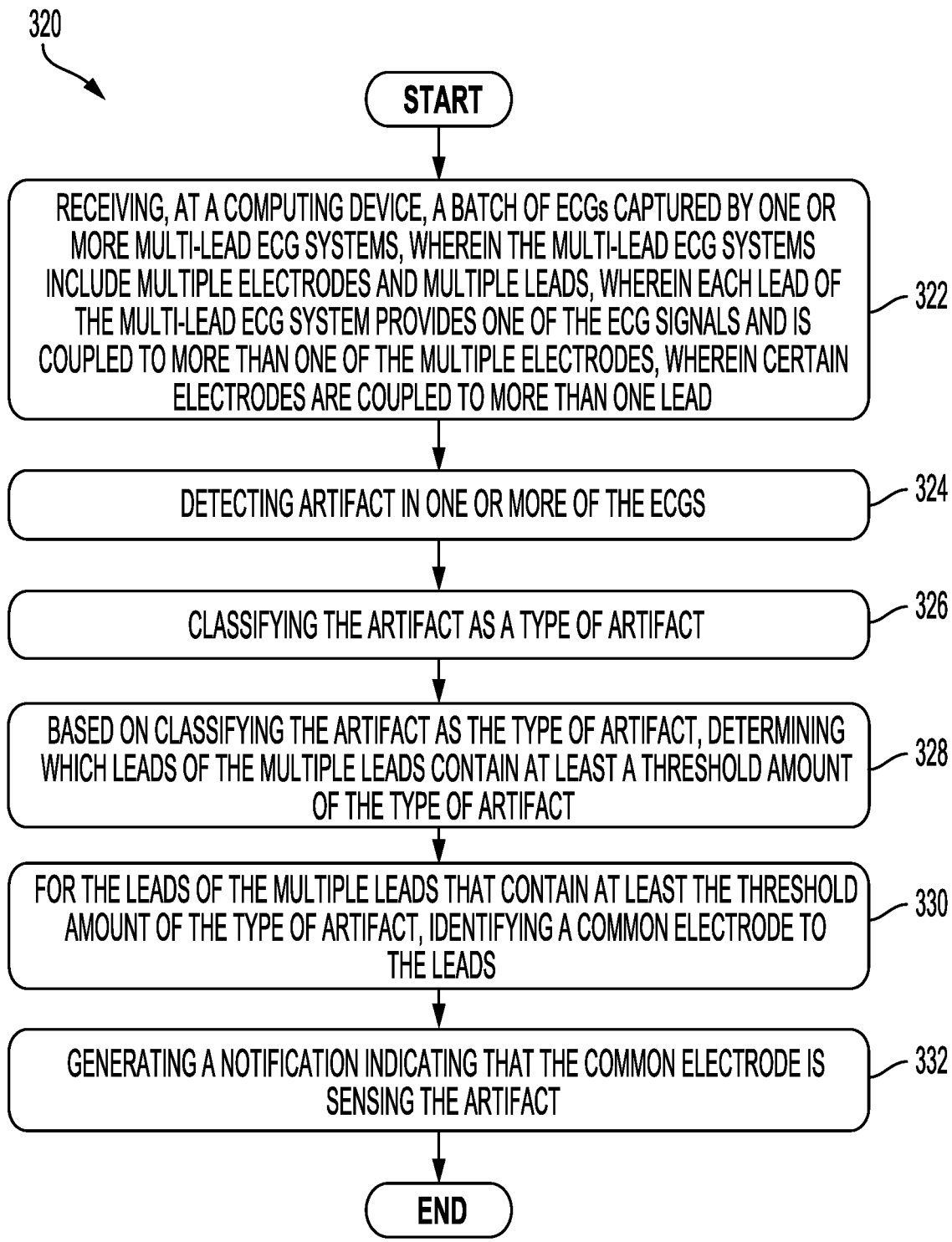
FIG. 4A shows a flowchart of another example of a method of analyzing electrocardiogram (ECG) signals, according to an example implementation.

FIG. 4A shows a flowchart of another example of a method 320 of analyzing electrocardiogram (ECG) signals, according to an example implementation. The method 320 may be executed by a computing device, which may be the ECG device 106 shown in FIG. 1, or a general computing device with a processor, and memory storing instructions executable by the processor for performing functions of the method 320.

At block 322, the method 320 includes receiving, at a computing device, a batch of ECGs captured by one or more multi-lead ECG systems, and the multi-lead ECG systems include multiple electrodes and multiple leads, where each lead of the multi-lead ECG system provides one of the ECG signals and is coupled to more than one of the multiple electrodes, and certain electrodes are coupled to more than one lead. At block 324, the method 300 includes detecting an artifact in one or more of the ECG signals. At block 326, the method 300 includes classifying the artifact as a type of artifact. At block 328, the method 300 includes based on classifying the artifact as the type of artifact, determining which leads of the multiple leads contain at least a threshold amount of the type of artifact. At block 330, the method 300 includes for the leads of the multiple leads that contain at least the threshold amount of the type of artifact, identifying a common electrode to the leads. At block 332, the method 300 includes generating a notification indicating that the common electrode is sensing the artifact.

In some examples, processing the batch of ECGs enables a statistical analysis to be performed. In particular examples, the method 320 can also include determining, for each electrode site of the multiple electrodes and each artifact type of the plurality of types of artifact, a proportion of the ECG signals in the batch that contain substantial artifact of the type of artifact sensed by the electrode, generating a second notification indicating the proportion, and determining a quality score of the batch of ECG signals based on the proportion. The quality score can be quantified, such as a percentage, or a qualitative score as well.

In another particular example, the method 320 can also include determining a frequency of occurrence of each type of artifact of the plurality of artifacts in the batch of ECG signals, generating a second notification indicating the frequency, and determining a quality score of the batch of ECG signals based on the frequency.

As a further particular example, the method 320 can also include determining a frequency of occurrence of lead reversal in the batch of ECG signals, generating a second notification indicating the frequency, and determining a quality score of the batch of ECG signals based on the frequency.

Figure 4B:
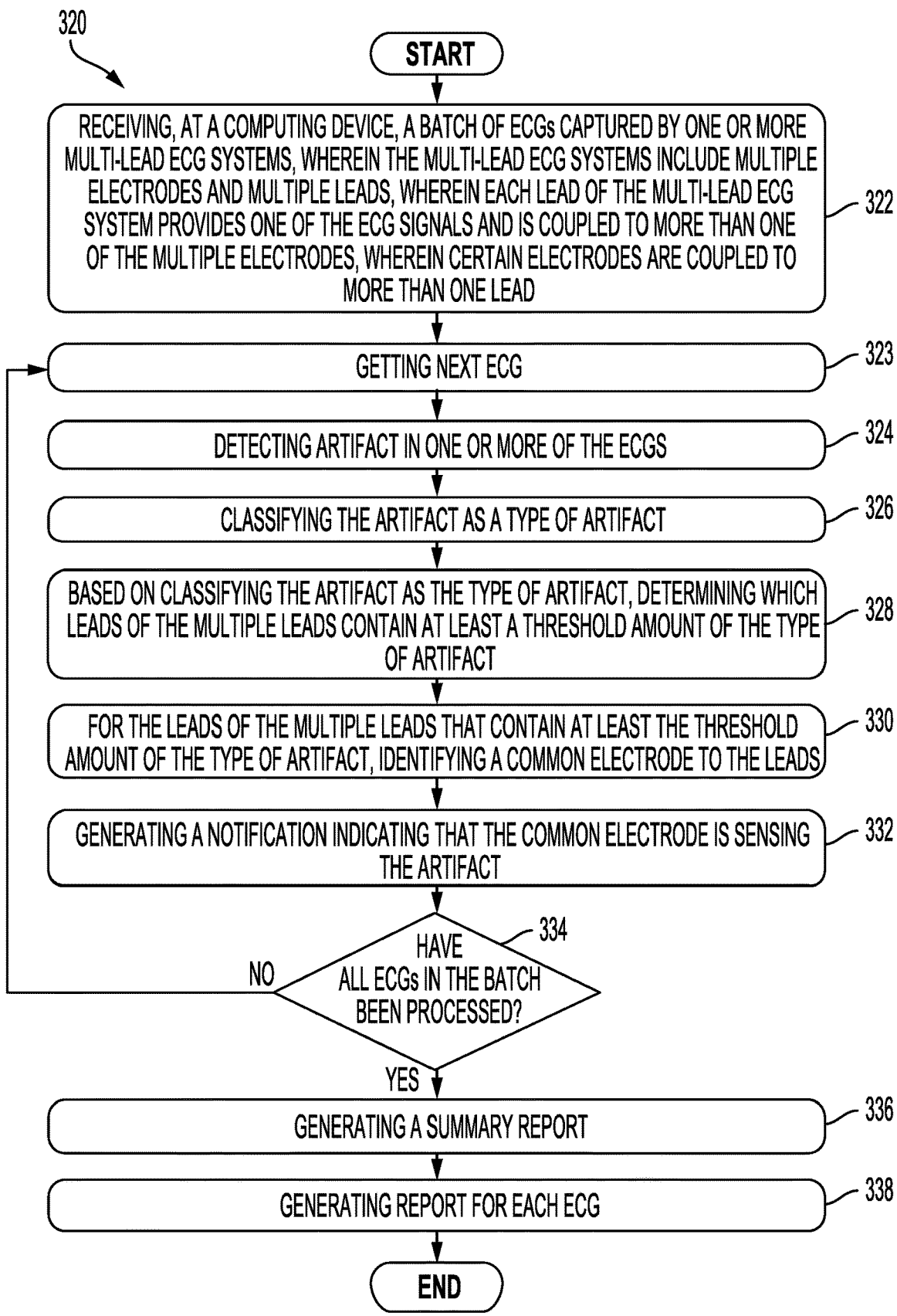
FIG. 4B shows a flowchart of yet another example of a method of analyzing electrocardiogram (ECG) signals, according to an example implementation.

FIG. 4B shows a flowchart of yet another example of the method 320 of analyzing electrocardiogram (ECG) signals, according to an example implementation. in FIG. 4B, the batch of ECGs is being processed one ECG at a time, iteratively, until all ECGs in the batch have been processed. Thus, after receiving the batch of ECGs at block 322, the method 320 can optionally include getting a next ECG, as shown at block 323. Then, after generating the notification at block 332, the method 320 may optionally include determining if all ECGs in the batch have been processed at block 334. If not, then the method 320 returns to block 323.

If yes at block 334, the method 320 optionally includes generating a summary report, at block 336. For example, the summary report can have a section reporting the proportion of ECGs that contained each type of ECG artifact that was found, and a section showing what was found for each ECG. Following, the method 320 optionally includes generating a report for each ECG to provide a detailed report, as shown at block 338.

Example ECG signals are shown in FIGS. 5-22, in which example artifact detections and classifications are described.

Figure 5:
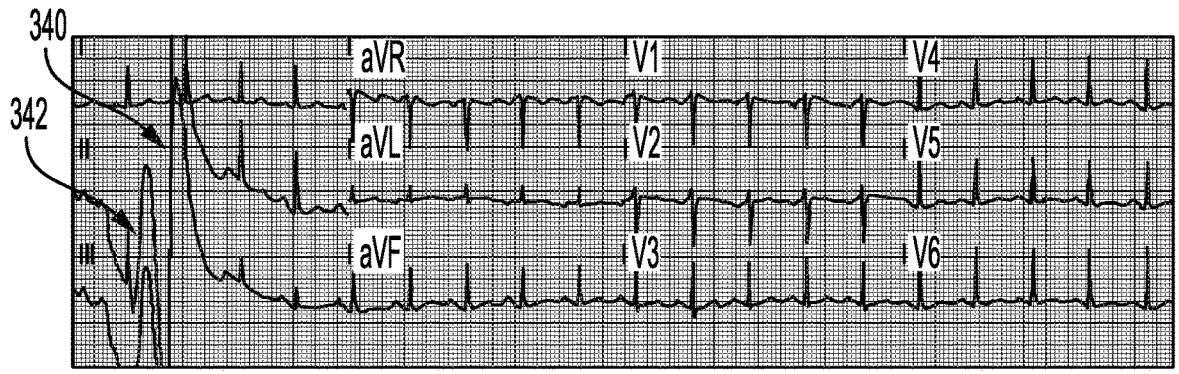
FIG. 5 is an example plot of ECG signals illustrating a poor contact artifact, according to an example implementation.

FIG. 5 is an example plot of ECG signals illustrating a poor contact artifact, according to an example implementation. The graph in FIG. 5 illustrates a plot of all 12 leads in a standard 12-lead ECG format, in which a ten second signal is capture for each lead, and then plotted for 2.5 seconds, such that the signals for Leads I-III during 0-2.5 seconds are shown, then the signals for Leads aVR, aVL, and aVF are shown during 2.5-5 seconds, then the signals for Leads V1-V3 are shown during 5-7.5 seconds, and lastly the signals for Leads V4-V6 are shown during 7.5-10 seconds.

From the above lead equations, it can be seen that if the LL electrode is picking up an artifact, it will be present to some degree in every lead except lead I. The lead equations also inform that if the LL electrode picks up artifact, the artifact will be present at full amplitude in leads II, III, and aVF, at half amplitude in leads aVR and aVL, and at one-third amplitude in all V leads. Therefore, the artifact from LL can be excessive in leads II, III, and aVF, but tolerable at lower amplitude in leads aVR and aVL and the V leads. And if artifact from LL is just enough to be intolerable in leads aVR and aVL, it may be tolerable at lower amplitude in the V leads.

Due to the view of the signals and timing shown in FIG. 5, the artifact is only present during the first 2.5 seconds, and will only be illustrated in the plot in Leads I-III. Since the artifact is seen in leads II and III but not seen in lead I, using the Equations (1)-(12), it can be determined that FIG. 5 illustrates an example of a poor contact artifact affecting just the LL electrode. In FIG. 5, the artifact is shown as an increase in amplitude in leads II and III outside of an acceptable range, as shown by artifacts 340 and 342.

Figure 6:
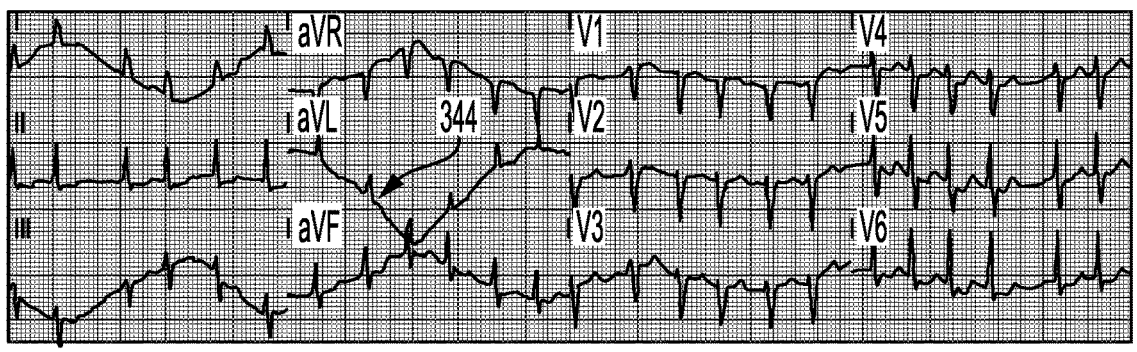
FIG. 6 is an example plot of ECG signals illustrating a motion artifact caused by respiration, according to an example implementation.

FIG. 6 is an example plot of ECG signals illustrating a motion artifact caused by respiration, according to an example implementation. The lead equations show that if the LA electrode is picking up artifact, the artifact will be present at full amplitude in leads I, III, and aVL, at half amplitude in leads aVR and aVF, and at one-third amplitude in the V leads. Artifact from the LA electrode will not be present in lead II. In FIG. 6, a sine wave artifact 344 is caused by respiration, and in this example, occurs in leads I and III but not II, so the common electrode in I and III is the LA electrode. Since the LA electrode is the positive electrode for lead I and the negative electrode for lead III, the artifact in lead III is inverted from the artifact in lead I. This artifact continues throughout the entire ten seconds, and thus, it affects 11 of 12 leads.

Figure 7:
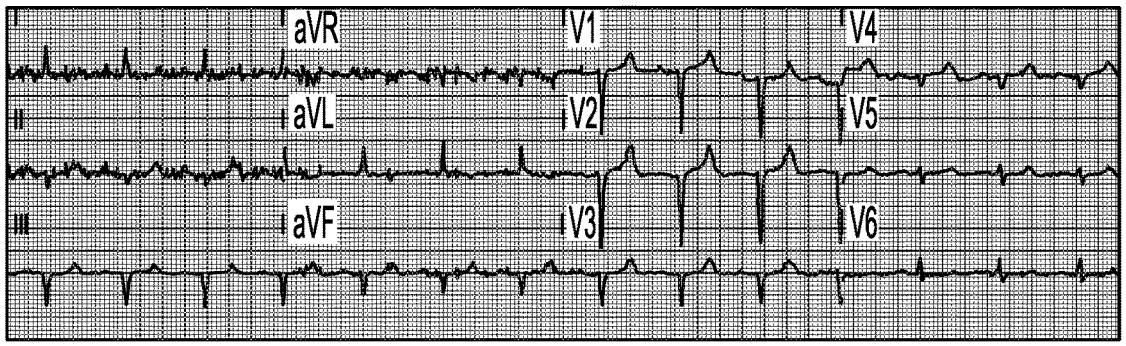
FIG. 7 is an example plot of ECG signals illustrating a muscle artifact, according to an example implementation.

FIG. 7 is an example plot of ECG signals illustrating muscle artifact, according to an example implementation. In FIG. 7, the muscle artifact is present in leads I and II but not III (as shown in the difference in amplitude below an expected threshold), and thus, it is substantially affecting only the RA electrode, which is the common electrode for leads I and II.

Figure 8:
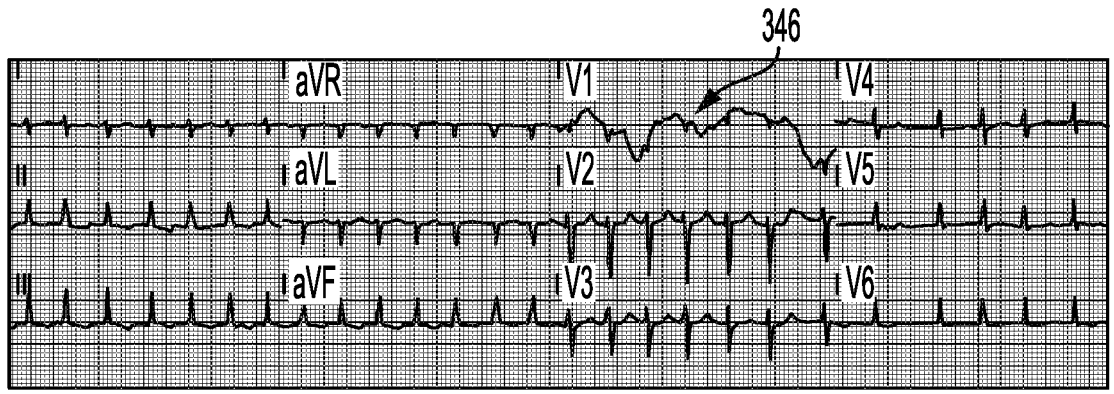
FIG. 8 is an example plot of ECG signals illustrating a motion artifact, according to an example implementation.

FIG. 8 is an example plot of ECG signals illustrating a motion artifact, according to an example implementation. In FIG. 8, an artifact 346 is in one V lead, as shown in the plot in V1. For the chest electrodes, the lead equations (Equations 7 through 13 above) show that artifact from a C electrode (e.g., C1) will affect only the associated V lead (e.g., V1). Thus, FIG. 8 is an example of motion artifact substantially affecting only the C1 electrode.

Figure 9:
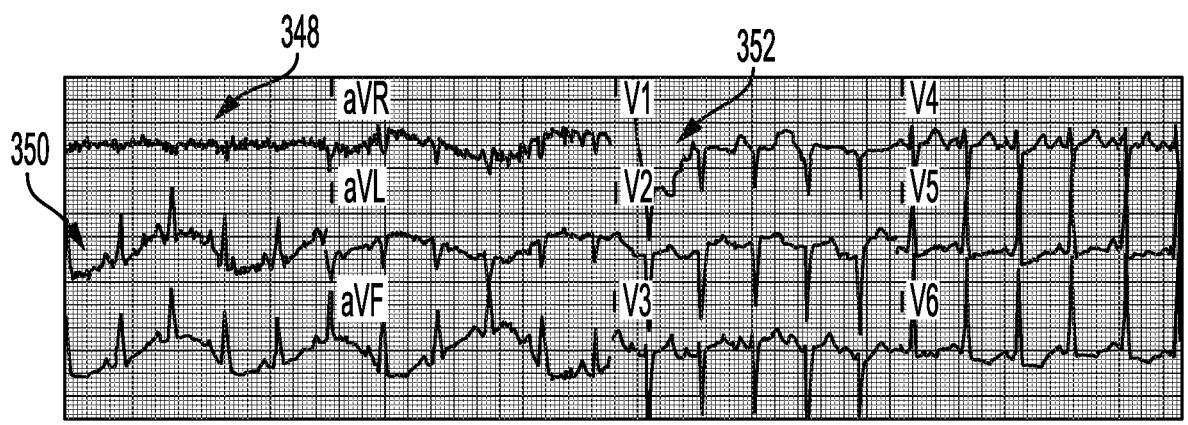
FIG. 9 is an example plot of ECG signals illustrating multiple artifacts, according to an example implementation.

FIG. 9 is an example plot of ECG signals illustrating multiple artifacts, according to an example implementation. In FIG. 9, there are three artifacts occurring on 3 different electrodes. For example, a muscle artifact 348 is affecting leads I and II but not III, and thus, is due to the RA electrode; a respiration baseline artifact 350 affecting II and III but not I, and thus, is due to the LL electrode; and a poor contact artifact 352 is present in a single V lead, V1, and thus, is due to the $V_1$ electrode. Thus, first, a type of artifact can be determined, and then it can be determined which electrodes are causing the problem based on the type of artifact.

Figure 10:
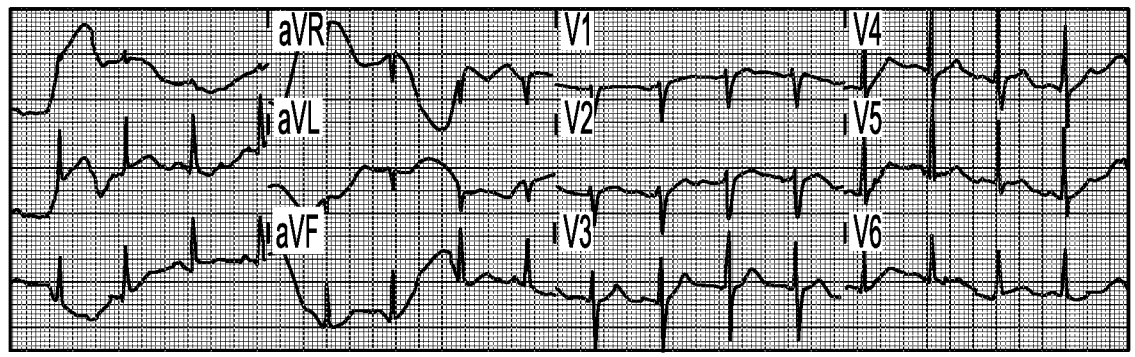
FIG. 10 is another example plot of ECG signals illustrating multiple artifacts, according to an example implementation.

FIG. 10 is another example plot of ECG signals illustrating artifact from multiple electrodes, according to an example implementation. When more than one limb electrode is picking up substantial artifact, then all limb leads will contain substantial artifact. It can sometimes be challenging to identify whether the artifact is being picked up by just LA and RA, or just LA and LL, or just RA and LL, or from all three of LA, RA, and LL. If matching artifact can be identified in two of leads I, II and III, then it can be determined that one particular limb electrode is one of the culprits. However, in that case it may be difficult to tell whether the additional artifact is coming from one or both of the other limb electrodes. Sometimes when there is substantial artifact in leads I, II, and III, the best that can be determined is that multiple (two to four) limb electrodes are culprit. In FIG. 10, such an example is shown with substantial motion artifact in leads I, IL, and III.

FIG. 11A is an example plot of ECG signals illustrating electromagnetic interference (EMI) artifact, according to an example implementation. In FIG. 11A, an ECG signal with EMI artifact is caused by use of a modified sine wave inverter in an ambulance. Note that the baseline is thicker in some leads, especially in leads I, III, aVL, V1, V4, and V6.

FIG. 11B is an example plot of a portion of lead III magnified illustrating the EMI artifact from FIG. 11A, according to an example implementation. In FIG. 11B, it can be seen that there are 180 cycles per 25 mm (each minor grid line is 1 mm), which is 180 cycles per second, or 180 Hz.

FIG. 11C is an example FFT plot of the ECG signals from FIG. 11A, according to an example implementation. In FIG. 11C, the FFT plot shows a spike at 180 Hz that indicates that there is a lot of energy in the ECG at 180 Hz. EMI at double and/or triple the line frequency (which is 60 Hz in this ECG) is characteristic of EMI from a modified sine wave inverter.

FIG. 12 is an example plot of ECG signals illustrating voltage spikes, according to an example implementation. In FIG. 12, an ECG with voltage spikes caused by atrial pacing (just prior to the P waves) and ventricular pacing (just prior to the QRS complexes) is illustrated. Showing the voltage spikes from pacemakers is clinically useful because it helps clinicians identify the ECG rhythm. Since pacemaker spikes are a signal of interest, they are not considered artifact.

FIG. 13 is an example plot of ECG signals illustrating stimulator artifact, according to an example implementation. In FIG. 13, an ECG with voltage spikes from a gastric stimulator. These spikes are considered artifact because they are unrelated to the heart and can make it difficult to determine the ECG rhythm.

Note that the lead equations do not contain limb electrode RL. The RL electrode is used to reduce common mode voltages picked up by the other electrodes. In modern ECG devices, the RL electrode is usually driven with the common mode voltage picked up by some of the other electrodes. Since the RL electrode is not used in the equations for the limb or chest leads, it will not be a culprit when at least one of the leads is substantially free of artifact. However, poor contact at the RL electrode or in its signal path, or extremely high skin impedance at the RL electrode, can result in substantial artifact in all leads.

The above examples provide insight into how to identify the culprit electrode when there is substantial artifact at electrodes, which commonly occurs in clinical practice. If there is substantial artifact in leads I and II, but little or none in lead III, then the RA electrode is picking up the artifact. If there is substantial artifact in leads I and III, but little or none in lead IL, then the LA electrode is picking up the artifact. If there is substantial artifact in leads II and III, but little or none in lead I, then the LL electrode is picking up the artifact, and so on.

It is easier to identify multiple C electrodes as being culprits for picking up artifact. For each V lead that has artifact that is different from that seen in other V leads, the associated C electrode is a culprit. If at least one V lead is substantially free of artifact, then any V lead that has substantial artifact has its associated C electrode as the culprit.

Figure 14:
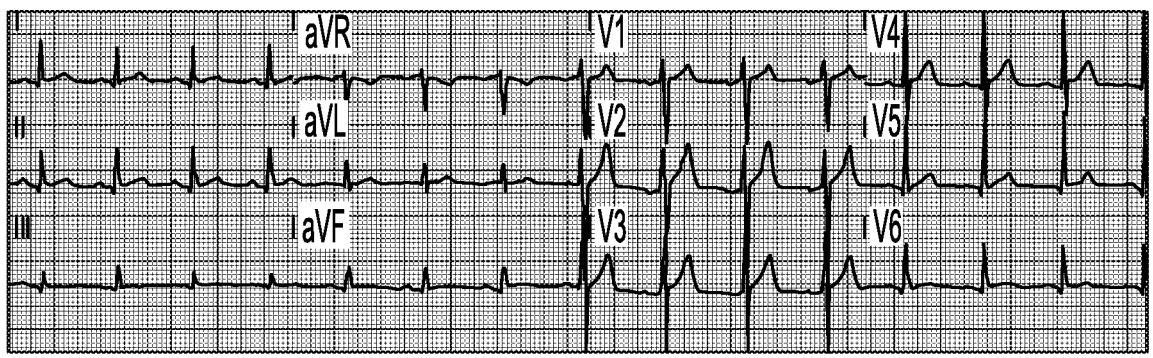
FIG. 14 is an example plot of ECG signals illustrating a correct leadwire placement, according to an example implementation.
Figure 15:
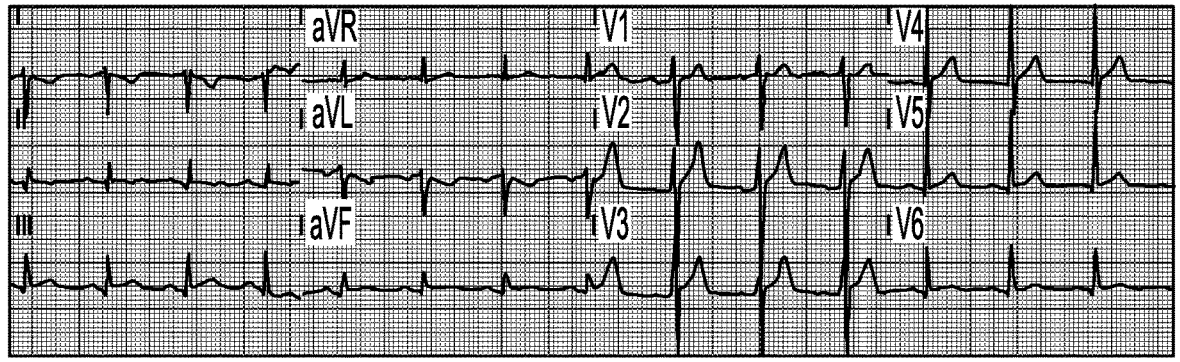
FIG. 15 is an example plot of ECG signals illustrating a leadwire reversal, according to an example implementation.

FIG. 14 is an example plot of ECG signals illustrating a correct leadwire placement, according to an example implementation. FIG. 15 is an example plot of ECG signals illustrating a leadwire reversal, according to an example implementation. In FIG. 15, there is an LA-RA reversal. The negative P wave, QRS complex, and T wave are caused by LA-RA leadwire reversal.

Figure 16:
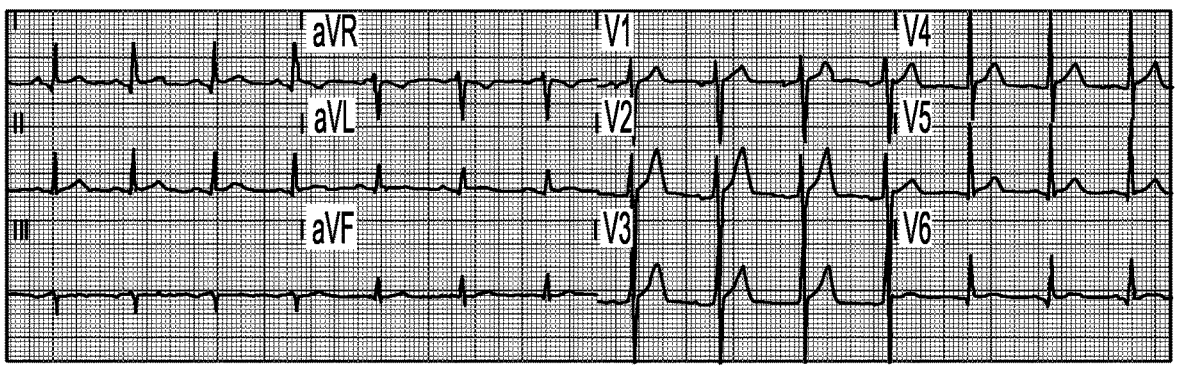
FIG. 16 is another example plot of ECG signals illustrating a leadwire reversal, according to an example implementation.

FIG. 16 is another example plot of ECG signals illustrating a leadwire reversal, according to an example implementation. In FIG. 16, there is an LA-LL reversal. A negative P wave and QRS complex in lead III suggests possible LA-LL reversal, however, physiological left axis deviation can also cause this. If the P wave is larger in lead I than in lead II that also suggests possible LA-LL reversal. It is often difficult to be sure whether there is LA-LL reversal, but when the ECG pattern suggests possible LA-LL reversal it can be useful to notify the user so that they can check the positions of the LA and LL leadwires. FIG. 16 shows an ECG from the same subject with LA-LL reversal, causing a negative P wave and QRS complex in lead III and a larger P wave in lead I than in lead II.

Figure 17:
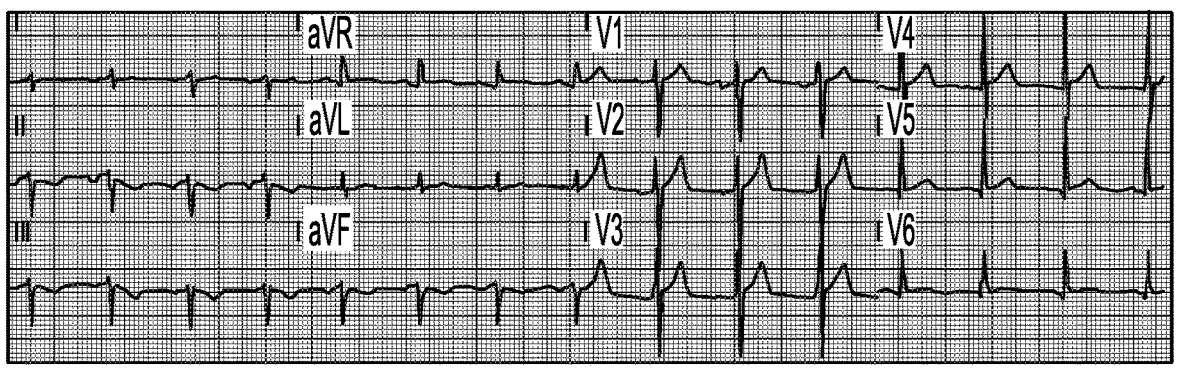
FIG. 17 is another example plot of ECG signals illustrating a leadwire reversal, according to an example implementation.

FIG. 17 is another example plot of ECG signals illustrating a leadwire reversal, according to an example implementation. In FIG. 17, there is an RA-LL reversal. A negative P wave and QRS complex in lead II is most likely caused by RA-LL reversal.

Figure 18:
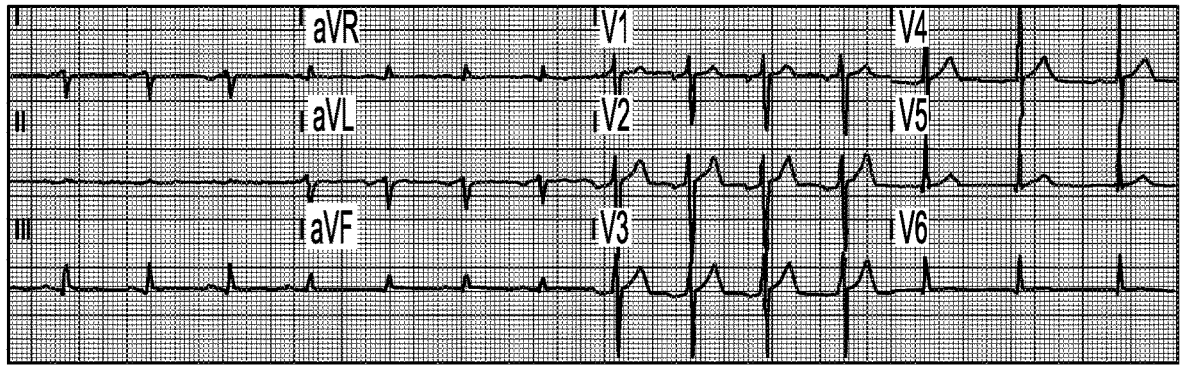
FIG. 18 is another example plot of ECG signals illustrating a leadwire reversal, according to an example implementation.

FIG. 18 is another example plot of ECG signals illustrating a leadwire reversal, according to an example implementation. In FIG. 18, there is an RA-RL reversal. If lead II has extremely low amplitude, RA-RL reversal is usually the cause.

Figure 19:
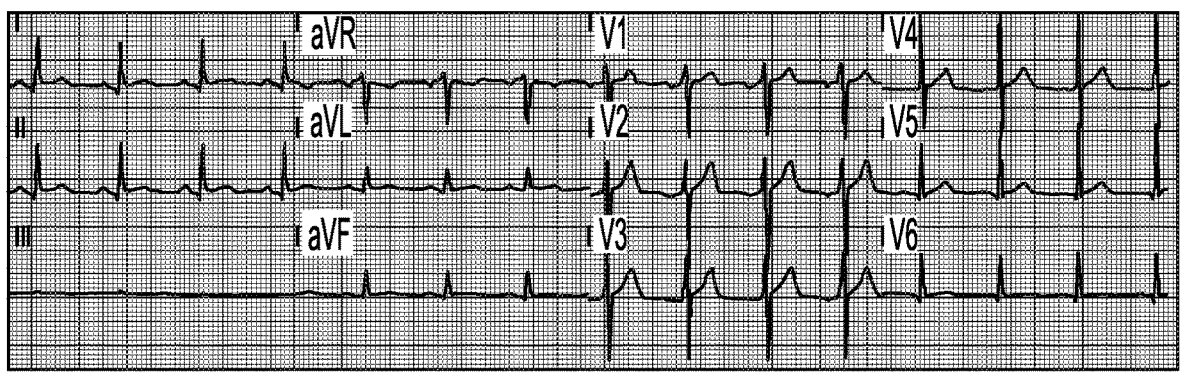
FIG. 19 is another example plot of ECG signals illustrating a leadwire reversal, according to an example implementation.

FIG. 19 is another example plot of ECG signals illustrating a leadwire reversal, according to an example implementation. In FIG. 19, there is an LA-RL reversal. If lead III has extremely low amplitude, LA-RL reversal is usually the cause.

Figure 20:
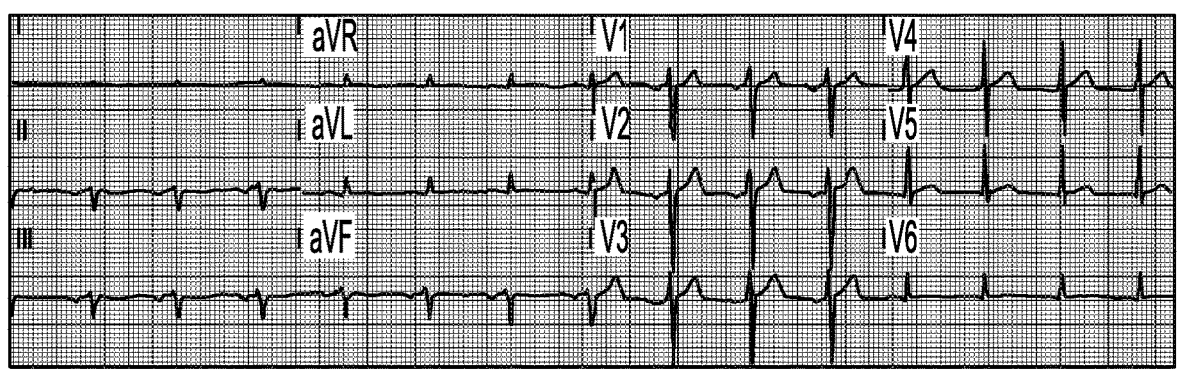
FIG. 20 is another example plot of ECG signals illustrating a leadwire reversal, according to an example implementation.

FIG. 20 is another example plot of ECG signals illustrating a leadwire reversal, according to an example implementation. In FIG. 20, there is an arm-leg leadwire reversal. If lead I has extremely low amplitude, it suggests the possibility of both RA-RL and LA-LL reversal.

Figure 21:
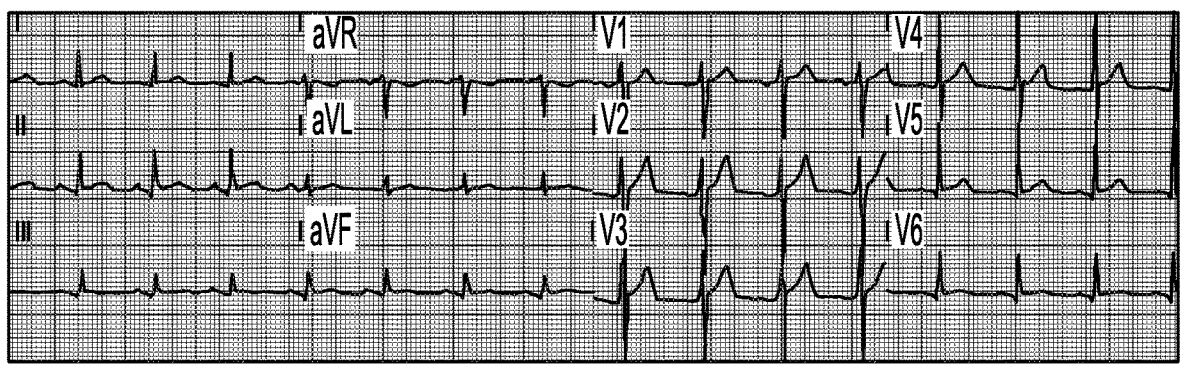
FIG. 21 is another example plot of ECG signals illustrating a leadwire reversal, according to an example implementation.

FIG. 21 is another example plot of ECG signals illustrating a leadwire reversal, according to an example implementation. In FIG. 21, there is an LL-RL reversal. Here, the LL-RL reversal has almost no effect on the ECG. It is almost impossible to detect, but it has no substantial effect on ECG interpretation. Therefore, there is no clinical need to detect LL-RL reversal. FIG. 21 illustrates an example plot with LL-RL reversal and the ECG is indistinguishable from the ECG in FIG. 14, which had correct leadwire placement.

Figure 22:
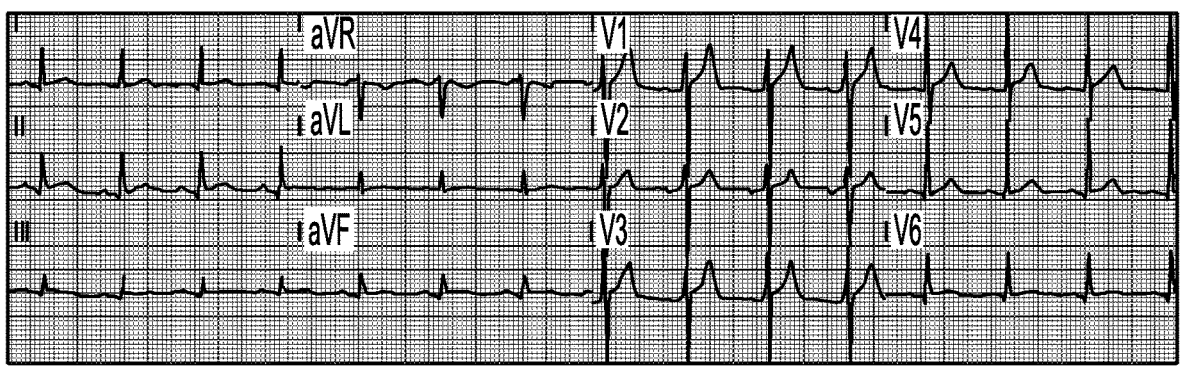
FIG. 22 is another example plot of ECG signals illustrating a leadwire reversal, according to an example implementation.

FIG. 22 is another example plot of ECG signals illustrating a leadwire reversal, according to an example implementation. In FIG. 22, an ECG plot is shown with C1-C2 reversal, causing the R wave to decrease from V1 to V2, then increase from V2 to V3. For chest electrode reversal, the R wave amplitude normally increases monotonically from lead V1 through about lead V4, then decreases monotonically to V6. When the R wave amplitude is larger, then smaller, then larger across three consecutive V leads, the most likely cause is reversal of the leadwire for the middle V electrode of the group and one of its adjacent V electrodes. S waves also have a typical progression, increasing in amplitude from lead V1 to V2, then decreasing monotonically in amplitude through V6. Myocardial infarction can cause loss of R wave amplitude in affected leads, affecting the R wave progression from V1 through V6, therefore normal R wave progression should not be expected if there has been a prior septal or anterior infarct.

Example methods described above provide numerous examples of how to detect artifacts of different types in different leads, and then use the Equations (1)-(12) to determine which electrodes are the cause of the artifact. Below is one example of a specific set of functions to programmatically follow. Initially, the ECG signals can be processed by looking at leads I-III, and performing an FFT on the signals to process the signals in the frequency domain. Any excessive amount of medium/high frequency artifact identified in leads I and II but not III, after processing through filters, can be an indication of a RA electrode problem since the RA electrode is common to leads I and II, but not III. Following, any medium and high frequency artifact identified can be characteristic of muscle artifact. Further, looking at leads I-III, any unusual low frequency artifact in leads II and III but not lead I is indicative of a LL electrode problem, since the LL electrode is common to leads II and III, but not lead I. In the FFT, any 60 Hz artifact is likely caused by power line interference, or any harmonic of 60 Hz, 120 Hz or 180 Hz may be caused by other equipment and is classified as EMI artifact. Next, signals from all leads are processed to identify extreme excursions, such as ECG signal outside of range of 5 mm, which are indicative of a poor contact artifact. This processing can continue through all types of artifact and ranges of expected values, as described herein, to filter out possible causes of problems.

Example methods and devices described herein are useful to device users who are acquiring the ECG to inform them of when leadwire reversal is suspected. That will provide actionable feedback to the device user so that they can check leadwire locations and take corrective action, if necessary, before acquiring a diagnostic ECG for interpretation. By providing actionable feedback to device users when substantial ECG artifact or leadwire reversal is present, the device users will likely obtain a high-quality ECG a greater proportion of the time than with a conventional ECG device that does not provide such feedback. Furthermore, the actionable feedback is likely to help device users obtain a high-quality ECG in less time than with a conventional ECG device. It is known that excessive ECG artifact during ECG monitoring can make it difficult or impossible for a care provider or an automated algorithm to determine the heart rhythm and rate. It is also known that excessive ECG artifact in a diagnostic ECG can make it difficult or impossible for a care provider or an automated algorithm to make measurements of the ECG and to interpret the ECG. Therefore, the examples herein will improve healthcare by allowing the care providers to more often and more quickly obtain a high-quality ECG.

The example methods and devices described herein may be used to continuously look for artifact or leadwire reversal in the ECG as it is being continuously acquired, or it may be used to look for artifact or leadwire reversal in a static snapshot of the ECG, such as an acquired ECG. By continuously looking for artifact or leadwire reversal as the ECG is continuously acquired, the artifact and leadwire reversal detectors can provide feedback to the device user as to whether the ECG currently has substantial artifact or leadwire reversal. As mentioned, that would allow the user to take corrective action to improve ECG quality before acquiring a snapshot of the ECG, such as a 12-lead ECG. By looking for artifact in an acquired ECG, such as a 12-lead ECG, the ECG report could include a statement about the ECG artifact if substantial artifact was detected. That would notify downstream care providers, such as hospital physicians, that the ECG measurements and interpretation may be affected by ECG artifact.

The example methods and devices can be used in an ECG monitor that can acquire more than one ECG lead simultaneously. The example methods and devices can also be used in a device that acquires more than 12 leads, such as a 15-lead or 18-lead diagnostic electrocardiograph. In such a device, the R wave and S wave progression normally continues past lead V6 to V7 through V9, and in the other direction from V1 to V3r through V6r (V1 is equivalent to V2r and V2 is equivalent to V1r). The example methods and devices can also be used by another system that does not acquire ECGs, but which allows ECGs to be viewed, printed, analyzed, or otherwise processed. In such a system, detection of ECG artifact or leadwire reversal can be useful for continuous improvement of ECG quality. In such a system, artifact detection or leadwire reversal detection may be accomplished on a single ECG, on all ECGs in a patient case, or on a batch of ECGs from an arbitrary time period. For example, analysis of two batches of ECGs could help show whether ECG quality is improved in the most recent batch of ECGs compared to a historical batch of ECGs.

Thus, implementations of this disclosure provide technological improvements that are particular to computer technology, for example, those concerning analysis of ECG signals. Computer-specific technological problems, such as processing and interpreting ECG signals in a proper manner even when artifact is present, can be wholly or partially solved by implementations of this disclosure. For example, implementation of this disclosure allows for artifact to be detected, and correction action to be taken in real-time, or during analysis of the ECG data, data that has artifact can be ignored and not processed for interpretation. As another example, if leadwire reversal is detected with high confidence, the leadwire reversal can be corrected prior to ECG analysis. Implementations of this disclosure can thus introduce new and efficient improvements in the ways in which ECG data is analyzed.

By the term "substantially" and "about" used herein, it is meant that the recited characteristic, parameter, or value need not be achieved exactly, but that deviations or variations, including for example, tolerances, measurement error, measurement accuracy limitations and other factors known to skill in the art, may occur in amounts that do not preclude the effect the characteristic was intended to provide.

Different examples of the system(s), device(s), and method(s) disclosed herein include a variety of components, features, and functionalities. It should be understood that the various examples of the system(s), device(s), and method(s) disclosed herein may include any of the components, features, and functionalities of any of the other examples of the system(s), device(s), and method(s) disclosed herein in any combination or any sub-combination, and all of such possibilities are intended to be within the scope of the disclosure.

The description of the different advantageous arrangements has been presented for purposes of illustration and description, and is not intended to be exhaustive or limited to the examples in the form disclosed. Many modifications and variations will be apparent to those of ordinary skill in the art. Further, different advantageous examples may describe different advantages as compared to other advantageous examples. The example or examples selected are chosen and described in order to best explain the principles of the examples, the practical application, and to enable others of ordinary skill in the art to understand the disclosure for various examples with various modifications as are suited to the particular use contemplated.

What is claimed is:

1. A method of analyzing electrocardiogram (ECG) signals, comprising:
   receiving, at an ECG device, ECG signals from a multi-lead ECG system, wherein the multi-lead ECG system includes multiple electrodes and multiple leads, wherein each lead of the multi-lead ECG system provides one of the ECG signals and is coupled to more than one of the multiple electrodes, wherein certain electrodes are coupled to more than one lead, wherein the ECG device combines voltage signals from the multiple electrodes in preset combinations to form the ECG signals;
   detecting multiple different artifacts in one or more of the ECG signals;
   classifying the multiple different artifacts as one of a plurality of types of artifact;
   based on classifying the multiple different artifacts as one of the plurality of types of artifact, mapping leads of the multiple leads that contain one of the multiple different artifacts to a respective one of the plurality of types of artifact so as to form groups of leads;
   for each group of the groups of leads of the multiple leads that contain one of the multiple different artifacts, the ECG device programmatically identifying a respective common electrode to the group of leads by utilizing the preset combinations of the voltage signals to derive the common electrode contributing to generation of the ECG signals provided by the leads of the multiple leads that contain one of the multiple different artifacts;
   generating a notification by the ECG device indicating that the respective common electrode for each group is sensing the artifact; and
   performing said detecting, classifying, mapping, identifying, and generating continuously as the ECG signals are being received.

2. The method of claim 1, wherein the receiving, at the ECG device, the ECG signals from the multi-lead ECG system comprises receiving the ECG signals from a 12-lead system with multiple limb leads, multiple augmented limb leads, and multiple precordial leads.

3. The method of claim 1, wherein the receiving, at the ECG device, the ECG signals from the multi-lead ECG system comprises receiving the ECG signals at the ECG device that includes a defibrillator.

4. The method of claim 1, further comprising:
generating a second notification by the ECG device indicating the type of artifact.

5. The method of claim 1, wherein the classifying of the artifact as the type of artifact comprises classifying the artifact as one of poor contact artifact, motion artifact, muscle artifact, electromagnetic interference (EMI) artifact, and electronic stimulator artifact.

6. The method of claim 1, further comprising:
identifying a pattern in the ECG signals by comparison of a P wave and a QRS complex in the ECG signals from the multiple leads; and
for the leads of the multiple leads in which the pattern is identified, identifying a leadwire reversal.

7. The method of claim 1, further comprising:
identifying an R wave amplitude change pattern in the ECG signals from a lead of the multiple leads that includes a pattern other than increasing monotonically from a first precordial lead to approximately a fourth precordial lead and then decreasing monotonically; and
for the lead of the multiple leads having the R wave amplitude change pattern other than increasing monotonically from the first precordial lead to the fourth precordial lead and then decreasing monotonically, identifying a leadwire reversal.

8. The method of claim 1, further comprising:
identifying an S wave amplitude change pattern in the ECG signals from a precordial lead of the multiple leads that includes a pattern other than first decreasing and then increasing; and
for the precordial lead of the multiple leads having the S wave amplitude change pattern other than first decreasing and then increasing, identifying a leadwire reversal.

9. The method of claim 1, further comprising:
generating a second notification by the ECG device indicating a leadwire reversal.

10. The method of claim 1, wherein the receiving, at the ECG device, the ECG signals from the multi-lead ECG system comprises receiving the ECG signals from a 12-lead system with multiple bipolar limb leads, multiple augmented limb leads, and multiple precordial leads, including a left arm (LA) leadwire, a right arm (RA) leadwire, a left leg (LL) leadwire, a right leg (RL) leadwire, and multiple precordial leadwires and,
wherein a type of leadwire reversal is one of:
LA-RA leadwire reversal;
LA-LL leadwire reversal;
RA-LL leadwire reversal;
RA-RL leadwire reversal;
LA-RL leadwire reversal;
arm-leg leadwire reversal; and
reversal of two precordial leadwires.

11. The method of claim 1, further comprising:
converting, by the ECG device, the ECG signals into a frequency domain to generate frequency signals; and
processing the frequency signals through a filter, based on the type of artifact, to determine which leads of the multiple leads contain the type of artifact.

12. The method of claim 1, wherein classifying the multiple different artifacts as a poor contact artifact comprises:
detecting at least one of a voltage signal above a threshold or a loss of a voltage signal from an ECG lead.

13. The method of claim 1, wherein classifying the multiple different artifacts as an electromagnetic interference (EMI) artifact comprises:

converting the ECG signals into a frequency domain to generate frequency signals; and
processing the frequency signals through a filter for identifying a spike at an EMI frequency level.

14. A non-transitory computer-readable medium having stored therein a plurality of executable instructions, which when executed by a computing device having a processor causes the computing device to perform functions comprising:
receiving ECG signals from a multi-lead ECG system, wherein the multi-lead ECG system includes multiple electrodes and multiple leads, wherein each lead of the multi-lead ECG system provides one of the ECG signals and is coupled to more than one of the multiple electrodes, wherein certain electrodes are coupled to more than one lead, wherein the computing device combines voltage signals from the multiple electrodes in preset combinations to form the ECG signals;
detecting multiple different artifacts in one or more of the ECG signals;
classifying the multiple different artifacts as one of a plurality of types of artifact;
based on classifying the multiple different artifacts as one of the plurality of types of artifact, mapping leads of the multiple leads that contain one of the multiple different artifacts to a respective one of the plurality of types of artifact so as to form groups of leads;
for each group of the groups of leads of the multiple leads that contain one of the multiple different artifacts, the computing device programmatically identifying a respective common electrode to the group of leads by utilizing the preset combinations of the voltage signals to derive the common electrode contributing to generation of the ECG signals provided by the leads of the multiple leads that contain one of the multiple different artifacts;
generating a notification indicating that the respective common electrodes for each group are sensing respective one of the plurality of types of artifact; and
performing said detecting, classifying, mapping, identifying, and generating continuously as the ECG signals are being received.

15. The non-transitory computer-readable medium of claim 14, wherein the functions further comprise:
generating a second notification indicating a leadwire reversal.

16. An electrocardiogram (ECG) device comprising:
a non-transitory computer-readable medium having stored therein a plurality of executable instructions; and
a processor adapted to execute the plurality of executable instructions to:
receive ECG signals from a multi-lead ECG system, wherein the multi-lead ECG system includes multiple electrodes and multiple leads, wherein each lead of the multi-lead ECG system provides one of the ECG signals and is coupled to more than one of the multiple electrodes, wherein certain electrodes are coupled to more than one lead, wherein the processor combines voltage signals from the multiple electrodes in preset combinations to form the ECG signals;
detect multiple different artifacts in one or more of the ECG signals;
classify the multiple different artifacts as one of a plurality of types of artifact;
based on classifying the multiple different artifacts as one of the plurality of types of artifact, map leads of the multiple leads that contain one of the multiple different artifacts to a respective one of the plurality of types of artifact so as to form groups of leads;

for each group of the groups of leads of the multiple leads that contain one of the multiple different artifacts, the processor programmatically identifying a respective common electrode to the group of leads by utilizing the preset combinations of the voltage signals to derive the common electrode contributing to generation of the ECG signals provided by the leads of the multiple leads that contain one of the multiple different artifacts;

generate a notification indicating that the respective common electrode for each group is sensing the artifact; and perform said detect, classify, map, identifying, and generate continuously as the ECG signals are being received.

17. A method of analyzing electrocardiograms (ECGs), comprising:

receiving, at a computing device, a batch of ECGs captured by one or more multi-lead ECG systems, wherein the multi-lead ECG systems include multiple electrodes and multiple leads, wherein each lead of the multi-lead ECG system provides one of the ECGs and is coupled to more than one of the multiple electrodes, wherein certain electrodes are coupled to more than one lead, wherein voltage signals are combined from the multiple electrodes in preset combinations to form the ECGs;

detecting multiple different artifacts in one or more of the ECG signals;

classifying the multiple different artifacts as one of a plurality of types of artifact;

based on classifying the multiple different artifacts as one of the plurality of types of artifact, mapping leads of the multiple leads that contain one of the multiple different artifacts to a respective one of the plurality of types of artifact so as to form groups of leads;

for each group of the groups of leads of the multiple leads that contain one of the multiple different artifacts, programmatically identifying a respective common electrode to the group of leads by utilizing the preset combinations of the voltage signals to derive the common electrode contributing to generation of the ECG signals provided by the leads of the multiple leads that contain one of the multiple different artifacts;

generating a notification indicating that the respective common electrode for each group is sensing the artifact; and performing said detecting, classifying, mapping, identifying, and generating continuously as the ECG signals are being received.

18. The method of claim 17, wherein classifying the artifact as the type of artifact comprises classifying the artifact as one of a plurality of types of artifact, and the method further comprises:

determining, for each electrode site of the multiple electrodes and each artifact type of the plurality of types of artifact, a proportion of the ECGs in the batch that contain artifact of the type of artifact sensed by the electrode;

generating a second notification indicating the proportion.

19. The method of claim 17, wherein classifying the artifact as the type of artifact comprises classifying the artifact as one of a plurality of types of artifact, and the method further comprises:

determining a frequency of occurrence of each type of artifact of the plurality of artifact in the batch of ECGs;

generating a second notification indicating the frequency.

20. The method of claim 17, further comprising:

determining a frequency of occurrence of lead reversal in the batch of ECGs;

generating a second notification indicating the frequency.

\* \* \* \* \*